US007772208B2

(12) United States Patent
Schinazi et al.

(10) Patent No.: US 7,772,208 B2
(45) Date of Patent: Aug. 10, 2010

(54) 2',3'-DIDEOXYNUCLEOSIDE ANALOGUES FOR THE TREATMENT OR PREVENTION OF *FLAVIVIRIDAE* INFECTIONS

(75) Inventors: Raymond Schinazi, Atlanta, GA (US); Robert Striker, Madison, WI (US); Junxing Shi, Duluth, GA (US)

(73) Assignees: Pharmasset, Inc., Princeton, NJ (US); Leland Stanford Junior University, Palo Alto, CA (US); Emory University, Atlanta, GA (US)

( * ) Notice: Subject to any disclaimer, the term of this patent is extended or adjusted under 35 U.S.C. 154(b) by 0 days.

(21) Appl. No.: 11/970,908

(22) Filed: Jan. 8, 2008

(65) Prior Publication Data

US 2008/0280846 A1   Nov. 13, 2008

Related U.S. Application Data

(63) Continuation of application No. 10/632,875, filed on Aug. 1, 2003, now abandoned.

(60) Provisional application No. 60/453,715, filed on Aug. 1, 2002.

(51) Int. Cl.
*A61K 31/7068* (2006.01)
*A61K 31/7072* (2006.01)
*C07H 19/10* (2006.01)
*C07H 19/06* (2006.01)

(52) U.S. Cl. .............................. 514/49; 514/50; 514/51; 514/52; 536/26.8; 536/28.5; 536/28.51; 536/28.52; 536/28.53; 536/28.54; 536/28.55

(58) Field of Classification Search .................. None
See application file for complete search history.

(56) References Cited

U.S. PATENT DOCUMENTS

| | | | |
|---|---|---|---|
| 3,798,209 | A | 3/1974 | Witkowski et al. |
| RE29,835 | E | 11/1978 | Witkowski et al. |
| 4,788,181 | A | 11/1988 | Driscoll et al. |
| 5,106,962 | A | 4/1992 | Amino et al. |
| 5,220,003 | A | 6/1993 | Jung et al. |
| 5,627,160 | A | 5/1997 | Lin et al. |
| 5,631,239 | A | 5/1997 | Lin et al. |
| 5,990,093 | A | 11/1999 | Schinazi et al. |
| 6,545,021 | B1 | 4/2003 | Mueller et al. |
| 6,777,395 | B2 | 8/2004 | Bhat et al. |
| 2002/0019363 | A1 | 2/2002 | Ismaili et al. |
| 2002/0147160 | A1 | 10/2002 | Bhat et al. |
| 2003/0008841 | A1 | 1/2003 | Devos et al. |
| 2003/0028013 | A1 | 2/2003 | Wang et al. |
| 2003/0050229 | A1 | 3/2003 | Sommadossi et al. |
| 2003/0060400 | A1 | 3/2003 | LaColla et al. |
| 2003/0083307 | A1 | 5/2003 | Devos et al. |
| 2003/0087873 | A1 | 5/2003 | Stuyver et al. |

FOREIGN PATENT DOCUMENTS

| | | |
|---|---|---|
| WO | WO 99/43691 | 9/1999 |
| WO | WO 00/26225 | 5/2000 |
| WO | WO 01/32153 A2 | 5/2001 |
| WO | WO 01/60315 A2 | 8/2001 |
| WO | WO 01/79246 A2 | 10/2001 |
| WO | WO 01/90121 A2 | 11/2001 |
| WO | WO 01/92282 A2 | 12/2001 |
| WO | WO 02/18404 A2 | 3/2002 |
| WO | WO 02/32920 A2 | 4/2002 |
| WO | WO 02/48165 A2 | 6/2002 |
| WO | WO 02/057287 A2 | 7/2002 |
| WO | WO 02/057425 A2 | 7/2002 |
| WO | WO 02/100415 A2 | 12/2002 |
| WO | WO 03/061385 A1 | 7/2003 |
| WO | WO 03/062255 A2 | 7/2003 |
| WO | WO 03/068162 A2 | 8/2003 |

OTHER PUBLICATIONS

Pickering et al., "The Synthesis of 4'-t-butylcarbamyl- and 4'-toluenesulphonamidyl-2',3'-dideoxy Pyrimidine Nucleoside Analogs" Nucleosides and Nucleotides (1994) vol. 13 No. 6&7, pp. 1493-1506.*

Mansour et al., "Anti-HIV and Anti-HBV Activities of L-2',3'-Dideoxynucleoside Analogues: ddC, 5FddC, 5-aza ddC, and ddG" Med Chem Res (1995) vol. 5 pp. 417-425.*

Gagnon, L. et al., "Immunomodulatory and antiviral activities of 2',3'-dideoxy-β-L-cytidine and 2',3'-dideoxy-β-L-5-fluorocytidine," *Immunopharmacology and Immunotoxicology*, vol. 17, No. 1, pp. 17-32 (1995).

Lin, T. et al., "Antiviral activity of 2',3'-dideoxy-β-L-5-fluorocytidine (β-L-FddC) and 2',3'-dideoxy-β-L-cytidine (β-L-ddC) against hepatitis B virus and human immunodeficiency virus type 1 in vitro," *Biochemical Pharmacology*, vol. 47, No. 2, pp. 171-174 (1994).

Locatelli, G. et al., "Hepatitis C Virus NS3 NTPase/Helicase: Different Stereoselectivity in Nucleoside Triphosphate Utilisation Suggests that NTPase and Helicase Activities are Coupled by a Nucleotide-dependent Rate Limiting Step," *J. Mol. Biol.*, vol. 313, pp. 683-694 (2001).

Beach, J. et al., "A Highly Stereoselective Synthesis of Anti-HIV 2',3'-Dideoxy- and 2',3'-Didehydro-2',3'-dideoxynucleosides," *J. Org. Chem.*, vol. 57, No. 14, pp. 3887-3894 (1992).

(Continued)

*Primary Examiner*—Shaojia Anna Jiang
*Assistant Examiner*—Eric S Olson
(74) *Attorney, Agent, or Firm*—Merchant & Gould, PC

(57) ABSTRACT

A method for the treatment or prevention of Flaviviridae infections, in particular, hepatitis C virus infection, in a host, and in particular, a human, is provided that includes administering an effective amount of a β-L- or β-D-2',3'-dideoxynucleoside or a pharmaceutically acceptable salt or prodrug thereof, optionally in a pharmaceutically acceptable diluent or excipient.

26 Claims, 5 Drawing Sheets

OTHER PUBLICATIONS

Davis, G., "Current Therapy for Chronic Hepatitis C," *Gastroenterology*, vol. 118, No. 2, Supplement, pp. S104-S114 (Feb. 2000).

Ferrari, E. et al., "Characterization of Soluble Hepatitis C Virus RNA-Dependent RNA Polymerase Expressed in *Escherichia coli*," *Journal of Virology*, vol. 73, No. 2, pp. 1649-1654 (Feb. 1999).

Kao, C. et al., "Template Requirements for RNA Synthesis by a Recombinant Hepatitis C Virus RNA-Dependent RNA Polymerase," *Journal of Virology*, vol. 74, No. 23, pp. 11121-11128 (Dec. 2000).

Lohmann, V. et al., "Biochemical and Kinetic Analyses of NS5B RNA-Dependent RNA Polymerase of the Hepatitis C Virus," *Virology*, vol. 249, pp. 108-118 (1998).

The Merck Index, 11th edition, S. Budavari, Ed., Merck & Co., Inc., Rahway, NJ, p. 1304, sections 8199 and 8200 (1989).

Okabe, M. et al., "Synthesis of the Dideoxynucleosides ddC and CNT from Glutamic Acid, Ribonolactone, and Pyrimidine Bases," *J. Org. Chem.*, vol. 53, No. 20, pp. 4780-4786 (1988).

\* cited by examiner

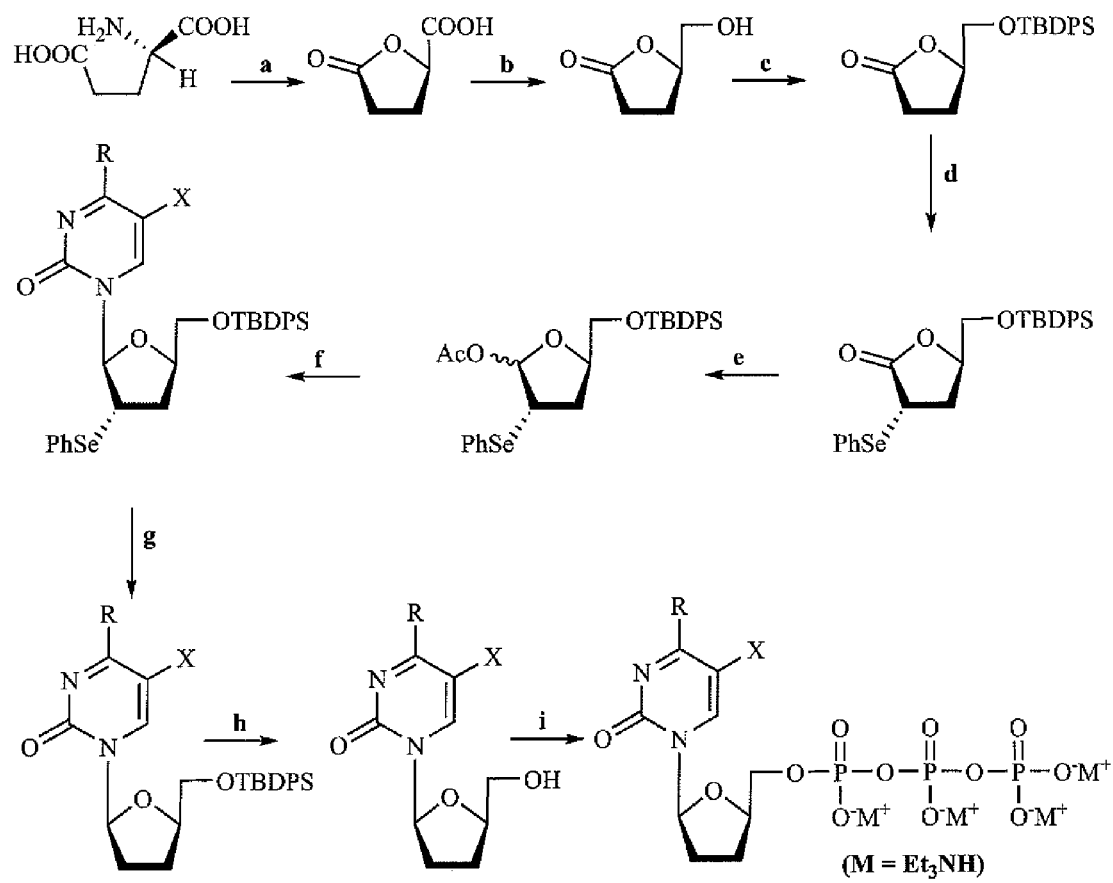

Keys: X = H or halogen (F, Cl, Br, I); R = NH$_2$ or OH; (a) NaNO$_2$, HCl, H$_2$O; (b) BH$_3$-SMe$_2$, THF; (c) DMF, TBDPSCl, imidazole; (D) THF, LiHMDS, TMSCl, PhSeBr; (e) i) DIBALH, toluene; ii) CH$_2$Cl$_2$, Pyr., DMAP, Ac$_2$O; (f) HMDS, (NH$_4$)$_2$SO$_4$, 5-FC, DME, TMSOTf; (g) Et$_3$B, Bu$_3$SnH, benzene; (h) THF, TBAF; (i) salicylchlorophosphite, DMF, Pyr., dioxane, (Bu$_3$NH)$_2$H$_2$P$_2$O$_7$, Bu$_3$N, I$_2$/H$_2$O/Pyr/THF

Fig. 1. Synthesis of L-2',3'-dideoxynucleosides and their triphosphates

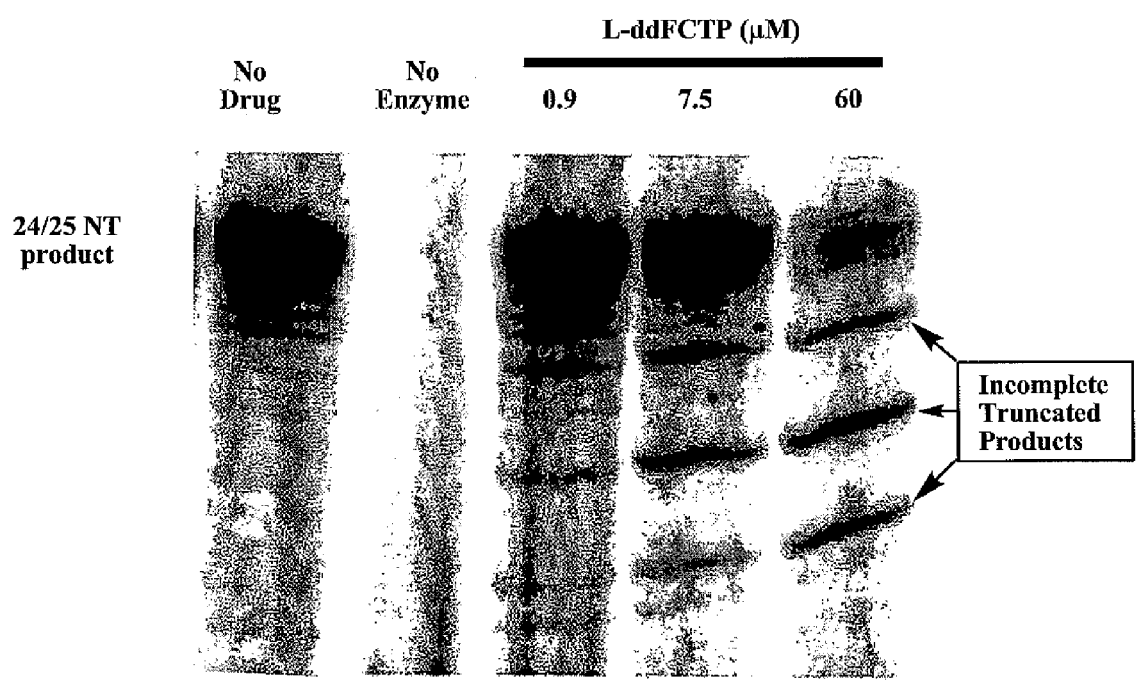
Fig. 2. Dose Response Data for L-ddFC Triphosphate with NS5B

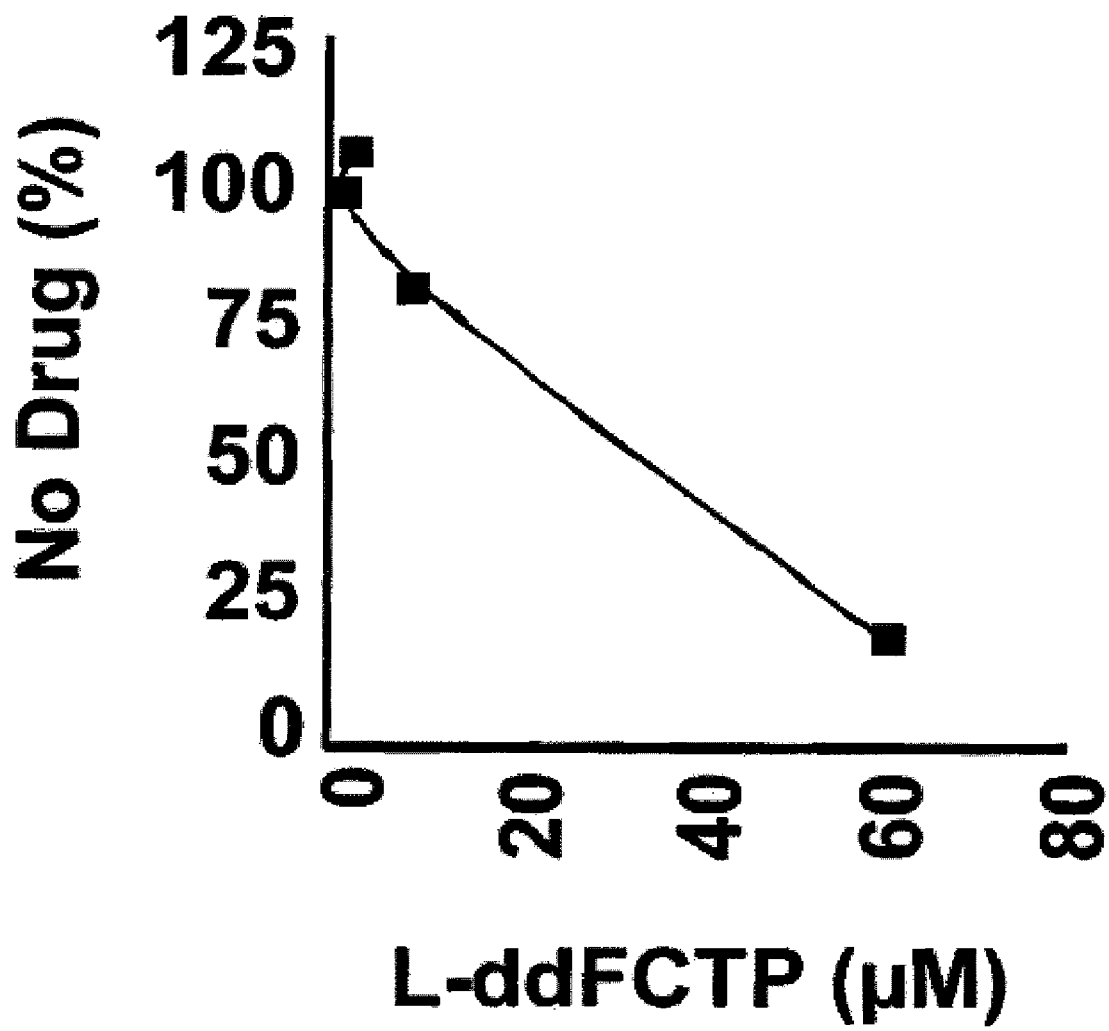
Fig. 3. Inhibition of Full-Length Product

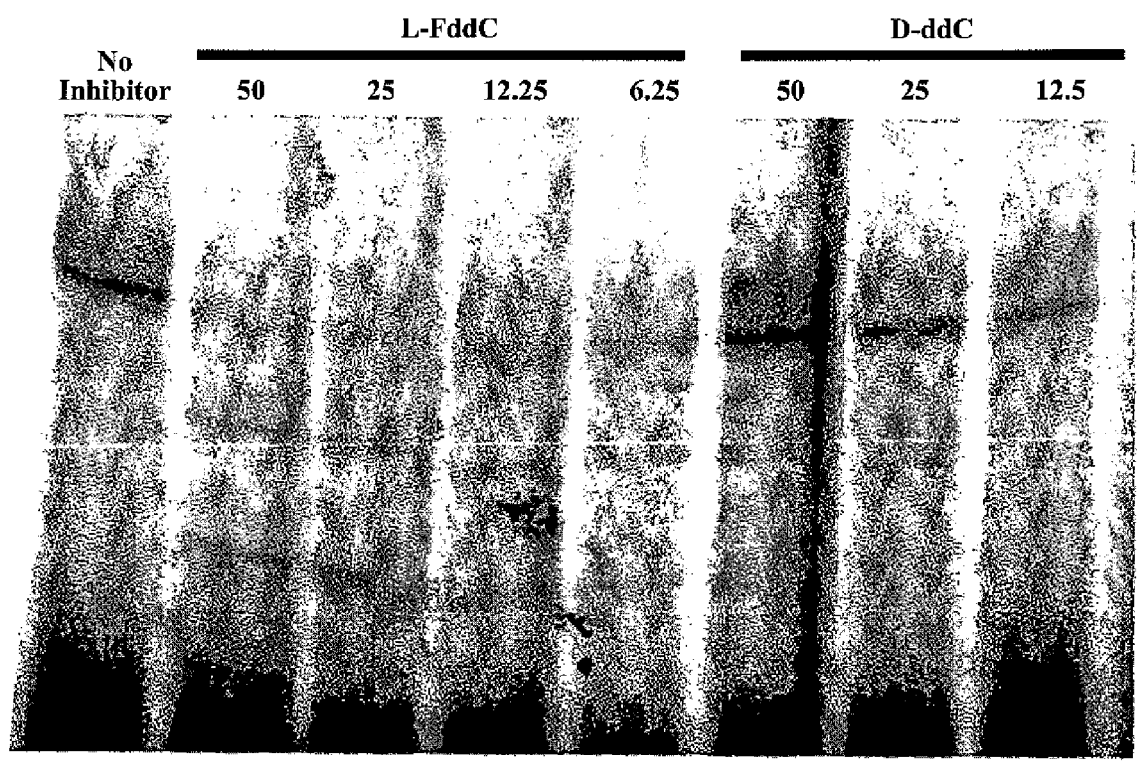
Fig. 4. Chain Termination of L-FddC versus D-ddC

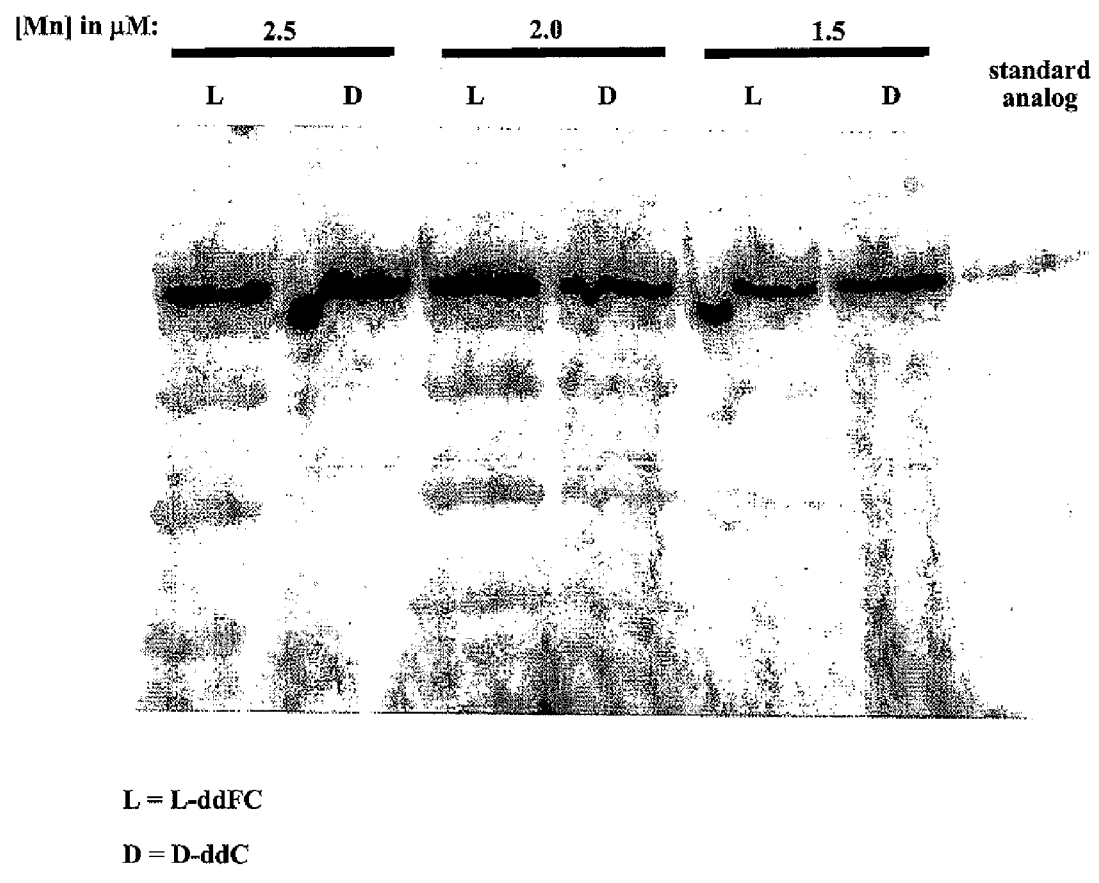
Fig. 5. Chain Termination of Dependent on Manganese

2',3'-DIDEOXYNUCLEOSIDE ANALOGUES FOR THE TREATMENT OR PREVENTION OF *FLAVIVIRIDAE* INFECTIONS

The present application is a continuation of U.S. patent application Ser. No. 10/632,875, filed Aug. 1, 2003, now abandoned which claims priority to U.S. Provisional Application No. 60/453,715, filed Aug. 1, 2002, the disclosure of which is incorporated herein.

FIELD OF THE INVENTION

The present invention is a method for the treatment or prevention of Flaviviridae infections using nucleoside analogues. More specifically, the invention describes 2',3'-dideoxynucleoside analogues, pharmaceutically acceptable salts or other derivatives thereof, and the use thereof in the treatment of a Flaviviridae viral infection, and, in particular, a hepatitis C virus (HCV) infection.

BACKGROUND OF THE INVENTION

Flaviviridae are a group of positive, single-stranded RNA viruses with genome sizes from 9 to 15 kb. They are enveloped viruses of approximately 40-50 nm. An overview of the Flaviviridae taxonomy is available from the International Committee for Taxonomy of Viruses. The group Flaviviridae consists of three genera.

1. Flaviviruses. This genus includes the Dengue virus group (Dengue virus, Dengue virus type 1, Dengue virus type 2, Dengue virus type 3, Dengue virus type 4), the Japanese encephalitis virus group (Alfuy virus, Japanese encephalitis virus, Kookaburra virus, Koutango virus, Kunjin virus, Murray Valley encephalitis virus, St. Louis encephalitis virus, Stratford virus, Usutu virus, West Nile virus), the Modoc virus group, the Rio Bravo virus group (Apoi virus, Rio Bravo virus, Saboya virus), the Ntaya virus group, the tick-born encephalitis group (tick-born encephalitis virus), the Tyuleniy virus group, Uganda S virus group and the Yellow Fever virus group. In addition to these major groups, there are other Flaviviruses that are unclassified.
2. Hepaciviruses. This genus contains only one species, the hepatitis C virus (HCV), which is composed of many clades, types and subtypes.
3. Pestiviruses. This genus includes bovine viral diarrhea virus-2 (BVDV-2), pestivirus type 1 (including BVDV), pestivirus type 2 (including hog cholera virus) and pestivirus type 3 (including border disease virus).

One of the most important Flaviviridae infections in humans is caused by the HCV. HCV is the second major cause of viral hepatitis, with an estimated 170 million carriers world-wide (World Health Organization; *Hepatitis C: global prevalence, Weekly Epidemiological Record*, 1997, 72, 341), 3.9 million of whom reside in the United States (Centers for Disease Control; unpublished data, http://www.cdc.gov/ncidod/diseases/hepatitis/heptab3.htm).

The genomic organization of the Flaviviridae share many common features. The HCV genome is often used as a model. HCV is a small, enveloped virus with a positive, single-stranded RNA genome of ~9.6 kb within the nucleocapsid.

The genome contains a single open reading frame (ORF), encoding a polyprotein of just over 3,000 amino acids, which is cleaved to generate the mature structural and nonstructural viral proteins. The ORF is flanked by 5'- and 3'-non-translated regions (NTRs) of a few hundred nucleotides in length, which are important for RNA translation and replication.

The translated polyprotein contains the structural core (C) and envelope proteins (E1, E2, p7) at the N-terminus, followed by the nonstructural proteins (NS2, NS3, NS4A, NS4B, NS5A, NS5B). The mature structural proteins are generated via cleavage by the host signal peptidase (see Hijikata M. et al. *Proc. Nat. Acad. Sci., USA*, 1991, 88, 5547; Hussy P. et al. *Virology*, 1996, 224, 93; Lin C. et al. *J. Virol.*, 1994, 68, 5063; Mizushima H. et al. *J. Virol.*, 1994, 68, 2731; Mizushima H. et al. *J. Virol.*, 1994, 68, 6215; Santolini E. et al. *J. Virol.*, 1994, 68, 3631; Selby M. J. et al. *Virology*, 1994, 204, 114; and Grakoui A. et al. *Proc. Nat. Acad. Sci., USA*, 1993, 90, 10538). The junction between NS2 and NS3 is autocatalytically cleaved by the NS2/NS3 protease (see Hijikata M. et al. *J. Virol.*, 1993, 67, 4665 and Bartenschlager R. et al. *J. Virol.*, 1994, 68, 5045), while the remaining four junctions are cleaved by the N-terminal serine protease domain of NS3, complexed with NS4A. (see Failla C. et al. *J. Virol.*, 1994, 68, 3753; Lin C. et al. *J. Virol.*, 1994, 68, 8147; Tanji Y. et al. *J. Virol.*, 1995, 69, 1575 and Tai C. L. et al. *J. Virol.*, 1996, 70, 8477) The NS3 protein also contains the nucleoside triphosphate (NTP)-dependent helicase activity, which unwinds duplex RNA during replication. The NS5B protein possesses RNA-dependent RNA polymerase (RDRP) activity (see Behrens S. E. et al. *EMBO J.*, 1996, 15, 12; Lohmann V. et al. *J. Virol.*, 1997, 71, 8416-8428 and Lohmann V. et al. *Virology* 1998, 249, 108), which is essential for viral replication. (Ferrari E. et al. *J. Virol.*, 1999, 73, 1649). Unlike HBV or HIV, no DNA is involved in the replication of HCV.

I. Treatment of HCV Infection with Ribavirin

Ribavirin (1-β-D-ribofuranosyl-1-1,2,4-triazole-3-carboxamide) is a synthetic, non-interferon-inducing, broad-spectrum antiviral nucleoside analog sold under the trade name Virazole (Merck Index, 11th edition, Editor: Budavari, S., Merck & Co., Inc., Rahway, N.J., p1304, 1989). U.S. Pat. No. 3,798,209 and RE29,835 disclose and claim Ribavirin. Ribavirin is structurally similar to guanosine, and has in vitro activity against several DNA and RNA viruses including Flaviviridae (Gary L. Davis. *Gastroenterology* 118:S104-S114, 2000).

Ribavirin reduces serum amino transferase levels to normal in 40% or patients, but it does not lower serum levels of HCV-RNA (Gary L. Davis. *Gastroenterology* 118:S104-S114, 2000). Thus, Ribavirin alone is not effective in reducing viral RNA levels. Additionally, Ribavirin has significant toxicity and is known to induce anemia.

Ribavirin is not approved for monotherapy against HCV. It has been approved in combination with interferon alpha-2a or interferon alpha-2b for the treatment of HCV.

II. Treatment of HCV Infection with Interferon

Interferons (IFNs) have been commercially available for the treatment of chronic hepatitis for nearly a decade. IFNs are glycoproteins produced by immune cells in response to viral infection. IFNs inhibit replication of a number of viruses, including HCV, and when used as the sole treatment for hepatitis C infection, IFN can in certain cases suppress serum HCV-RNA to undetectable levels. Additionally, IFN can normalize serum amino transferase levels. Unfortunately, the effect of IFN is temporary and a sustained response occurs in only 8%-9% of patients chronically infected with HCV (Gary L. Davis. *Gastroenterology* 118: S104-S114, 2000). Most patients, however, have difficulty tolerating interferon treatment, which causes severe flu-like symptoms, weight loss, and lack of energy and stamina.

A number of patents disclose Flaviviridae, including HCV, treatments, using interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon alpha for the treatment of infectious diseases including HCV. U.S. Pat. No. 5,849,696 to Chretien et al. discloses the use of thymosins, alone or in combination with interferon, for treating HCV. U.S. Pat. No. 5,830,455 to Valtuena et al. discloses a combination HCV therapy employing interferon and a free radical scavenger. U.S. Pat. No. 5,738,845 to Imakawa discloses the use of human interferon tau proteins for treating HCV. Other interferon-based treatments for HCV are disclosed in U.S. Pat. No. 5,676,942 to Testa et al., U.S. Pat. No. 5,372,808 to Blatt et al., and U.S. Pat. No. 5,849,696. A number of patents also disclose pegylated forms of interferon, such as, U.S. Pat. Nos. 5,747,646, 5,792,834 and 5,834,594 to Hoffmann-La Roche Inc; PCT Publication No. WO 99/32139 and WO 99/32140 to Enzon; WO 95/13090 and U.S. Pat. Nos. 5,738,846 and 5,711,944 to Schering; and U.S. Pat. No. 5,908,621 to Glue et al.

Interferon alpha-2a and interferon alpha-2b are currently approved as monotherapy for the treatment of HCV. ROFERON®-A (Roche) is the recombinant form of interferon alpha-2a. PEGASYS® (Roche) is the pegylated (i.e. polyethylene glycol modified) form of interferon alpha-2a. INTRON®A (Schering Corporation) is the recombinant form of Interferon alpha-2b, and PEG-INTRON® (Schering Corporation) is the pegylated form of interferon alpha-2b.

Other forms of interferon alpha, as well as interferon beta, gamma, tau and omega are currently in clinical development for the treatment of HCV. For example, INFERGEN (interferon alphacon-1) by InterMune, OMNIFERON (natural interferon) by Viragen, ALBUFERON by Human Genome Sciences, REBIF (interferon beta-1a) by Ares-Serono, Omega Interferon by BioMedicine, Oral Interferon Alpha by Amarillo Biosciences, and interferon gamma, interferon tau, and interferon gamma-1b by InterMune are in development.

III. Combination of Interferon and Ribavirin

The current standard of care for chronic hepatitis C is combination therapy with an alpha interferon and ribavirin. The combination of interferon and ribavirin for the treatment of HCV infection has been reported to be effective in the treatment of interferon naïve patients (Battaglia, A. M. et al., *Ann. Pharmacother.* 34:487-494, 2000), as well as for treatment of patients when histological disease is present (Berenguer, M. et al. *Antivir. Ther.* 3(Suppl. 3):125-136, 1998). Studies have show that more patients with hepatitis C respond to pegylated interferon-alpha/ribavirin combination therapy than to combination therapy with unpegylated interferon alpha. However, as with monotherapy, significant side effects develop during combination therapy, including hemolysis, flu-like symptoms, anemia, and fatigue. (Gary L. Davis. *Gastroenterology* 118:S104-S114, 2000).

Combination therapy with PEG-INTRON® (peginterferon alpha-2b) and REBETOL® (Ribavirin, USP) Capsules is available from Schering Corporation. REBETOL® (Schering Corporation) has also been approved in combination with INTRON® A (Interferon alpha-2b, recombinant, Schering Corporation). Roche's PEGASYS® (pegylated interferon alpha-2a) and COPEGUS® (ribavirin) are also approved for the treatment of HCV.

PCT Publication Nos. WO 99/59621, WO 00/37110, WO 01/81359, WO 02/32414 and WO 03/024461 by Schering Corporation disclose the use of pegylated interferon alpha and ribavirin combination therapy for the treatment of HCV. PCT Publication Nos. WO 99/15194, WO 99/64016, and WO 00/24355 by Hoffmann-La Roche Inc also disclose the use of pegylated interferon alpha and ribavirin combination therapy for the treatment of HCV.

IV. Additional References Disclosing Methods to Treat HCV Infections

A number of HCV treatments are reviewed by Bymock et al. in *Antiviral Chemistry & Chemotherapy,* 11:2; 79-95 (2000).

Several substrate-based NS3 protease inhibitors have been identified in the literature, in which the scissile amide bond of a cleaved substrate is replaced by an electrophile, which interacts with the catalytic serine. Attwood et al. (1998) Antiviral peptide derivatives, 98/22496; Attwood et al. (1999), Antiviral Chemistry and Chemotherapy 10.259-273; Attwood et al. (1999) Preparation and use of amino acid derivatives as antiviral agents, German Patent Publication DE 19914474; Tung et al. (1998) Inhibitors of serine proteases, particularly hepatitis C virus NS3 protease, WO 98/17679. The reported inhibitors terminate in an electrophile such as a boronic acid or phosphonate. Llinas-Brunet et al. (1999) Hepatitis C inhibitor peptide analogues, WO 99/07734. Two classes of electrophile-based inhibitors have been described, alphaketoamides and hydrazinoureas.

The literature has also described a number of non-substrate-based inhibitors. For example, evaluation of the inhibitory effects of 2,4,6-trihydroxy-3-nitro-benzamide derivatives against HCV protease and other serine proteases has been reported. Sudo, K. et al., (1997) *Biochemical and Biophysical Research Communications,* 238:643-647; Sudo, K. et al. (1998) *Antiviral Chemistry and Chemotherapy* 9:186. Using a reverse-phase HPLC assay, the two most potent compounds identified were RD3-4082 and RD3-4078, the former substituted on the amide with a 14-carbon chain and the latter processing a para-phenoxyphenyl group.

Thiazolidine derivatives have been identified as micromolar inhibitors, using a reverse-phase HPLC assay with an NS3/4A fusion protein and NS5A/5B substrate. Sudo, K. et al. (1996) *Antiviral Research* 32:9-18. Compound RD-1-6250, possessing a fused cinnamoyl moiety substituted with a long alkyl chain, was the most potent against the isolated enzyme. Two other active examples were RD4 6205 and RD4 6193.

Other literature reports screening of a relatively small library using an ELISA assay and the identification of three compounds as potent inhibitors, a thiazolidine and two benzanilides. Kakiuchi N. et al. *J. EBS Letters* 421:217-220; Takeshita N. et al., *Analytical Biochemistry* 247:242-246, 1997. Several U.S. patents disclose protease inhibitors for the treatment of HCV. For example, U.S. Pat. No. 6,004,933 to Spruce et al. discloses a class of cysteine protease inhibitors for inhibiting HCV endopeptidase 2. U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor. The use of restriction enzymes to treat HCV is disclosed in U.S. Pat. No. 5,538,865 to Reyes et al.

Isolated from the fermentation culture broth of *Streptomyces* sp., Sch 68631, a phenan-threnequinone, possessed micromolar activity against HCV protease in a SDS-PAGE and autoradiography assay. Chu M. et al., *Tetrahedron Letters* 37:7229-7232, 1996. In another example by the same authors, Sch 351633, isolated from the fungus *Penicillium griscofulvum,* demonstrated micromolar activity in a scintillation proximity assay. Chu M. et al., *Bioorganic and Medicinal Chemistry Letters* 9:1949-1952. Nanomolar potency against the HCV NS3 protease enzyme has been achieved by the design of selective inhibitors based on the macromolecule eglin c. Eglin c, isolated from the leech, is a potent inhibitor of several serine proteases such as *S. griseus* proteases A and B, α-chymotrypsin, chymase and subtilisin. Qasim M. A. et al., *Biochemistry* 36:1598-1607, 1997.

HCV helicase inhibitors have also been reported. U.S. Pat. No. 5,633,358 to Diana G. D. et al.; PCT Publication No. WO 97/36554 of Diana G. D. et al. There are a few reports of HCV polymerase inhibitors: some nucleotide analogues, gliotoxin and the natural product cerulenin. Ferrari R. et al., *Journal of Virology* 73:1649-1654, 1999; Lohmann V. et al., *Virology* 249:108-118, 1998.

Antisense phosphorothioate oligodeoxynucleotides complementary to sequence stretches in the 5'-non-coding region of the HCV, are reported as efficient inhibitors of HCV gene expression in in vitro translation and HepG2 HCV-luciferase cell culture systems. Alt M. et al., *Hepatology* 22:707-717, 1995. Recent work has demonstrated that nucleotides 326-348 comprising the 3'-end of the NCR and nucleotides 371-388 located in the core coding region of the HCV RNA are effective targets for antisense-mediated inhibition of viral translation. Alt M. et al., *Archives of Virology* 142:589-599, 1997. U.S. Pat. No. 6,001,990 to Wands et al discloses oligonucleotides for inhibiting the replication of HCV. PCT Publication No. WO 99/29350 discloses compositions and methods of treatment for hepatitis C infection comprising the administration of antisense oligonucleotides that are complementary and hybridizable to HCV RNA. U.S. Pat. No. 5,922,857 to Han et al. disclose nucleic acids corresponding to the sequence of the pestivirus homology box IV area for controlling the translation of HCV. Antisense oligonucleotides as therapeutic agents have been recently reviewed (Galderisi U. et al., *Journal of Cellular Physiology* 181:251-257, 1999).

Other compounds have been reported as inhibitors of IRES-dependent translation in HCV. Japanese Patent Publication JP-08268890 of Ikeda N et al.; Japanese Patent Publication JP-10101591 of Kai, Y. et al. Nuclease-resistant ribozymes have been targeted at the IRES and recently reported as inhibitors in an HCV-poliovirus chimera plaque assay. Maccjak D. J. et al., Hepatology 30 abstract 995, 1999. The use of ribozymes to treat HCV is also disclosed in U.S. Pat. No. 6,043,077 to Barber et al., and U.S. Pat. Nos. 5,869,253 and 5,610,054 to Draper et al.

Other patents disclose the use of immune system potentiating compounds for the treatment of HCV. For example, U.S. Pat. No. 6,001,799 to Chretien et al. discloses a method of treating HCV in non-responders to interferon treatment by administering an immune system-potentiating dose of thymosin or a thymosin fragment. U.S. Pat. Nos. 5,972,347 to Eder et al. and 5,969,109 to Bona et al. disclose antibody-based treatments for HCV infection.

U.S. Pat. No. 6,034,134 to Gold et al. discloses certain NMDA receptor agonists having immunomodulatory, antimalarial, anti-Borna virus and anti-HCV activities. The disclosed NMDA receptor agonists belong to a family of 1-amino-alkylcyclohexanes. U.S. Pat. No. 6,030,960 to Morris-Natschke et al. discloses the use of certain alkyl lipids to inhibit the production of hepatitis-induced antigens, including those produced by HCV. U.S. Pat. No. 5,922,757 to Chojkier et al. discloses the use of vitamin E and other antioxidants to treat hepatic disorders including HCV. U.S. Pat. No. 5,858,389 to Elsherbi et al. discloses the use of squalene for treating HCV infection. U.S. Pat. No. 5,849,800 to Smith et al discloses the use of amantadine for treatment of HCV infection. U.S. Pat. No. 5,846,964 to Ozeki et al. discloses the use of bile acids for treating HCV infection. U.S. Pat. No. 5,491,135 to Blough et al. discloses the use of N-(phosphonoacetyl)-L-aspartic acid to treat flavivirus infections, such as HCV infection.

Other compounds proposed for treating HCV infection include plant extracts (U.S. Pat. No. 5,837,257 to Tsai et al., U.S. Pat. No. 5,725,859 to Omer et al., and U.S. Pat. No. 6,056,961), piperidenes (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.).

Other agents for the treatment of HCV infection include PEGASYS (pegylated interferon alfa-2a) by Roche, INFERGEN (interferon alfacon-1) by InterMune, OMNIFERON (natural interferon) by Viragen, ALBUFERON by Human Genome Sciences, REBIF (interferon beta-1a) by Ares-Serono, omega Interferon by BioMedicine, Oral Interferon Alpha by Amarillo Biosciences, Interferon gamma-1b by InterMune, Interleukin-10 by Schering-Plough, IP-501 by Interneuron, Merimebodib VX-497 by Vertex, AMANTADINE (Symmetrel) by Endo Labs Solvay, HEPTAZYME by RPI, IDN-6556 by Idun Pharma., XTL-002 by XTL., HCV/MF59 by Chiron, CIVACIR by NABI, LEVOVIRIN by ICN, VIRAMIDINE by ICN, ZADAXIN (thymosin alfa-1) by Sci Clone, CEPLENE (histamine dihydrochloride) by Maxim, VX 950/LY 570310 by Vertex/Eli Lilly, ISIS 14803 by Isis Pharmaceutical/Elan, IDN-6556 by Idun Pharmaceuticals, Inc. and JTK 003 by AKROS Pharma.

BioChem Pharma Inc. disclosed the use of various 1,3-dioxolane nucleosides for the treatment of a Flaviviridae infection in International Publication No. WO 01/32153.

BioChem Pharma Inc. also disclosed various other 2'-halo, 2'-hydroxy and 2'-alkoxy nucleosides for the treatment of a Flaviviridae infection in International Publication No. WO 01/60315.

Idenix Pharmaceuticals, Ltd. discloses branched nucleosides, and their use in the treatment of HCV and flaviviruses and pestiviruses in International Publication Nos. WO 01/90121 and WO 01/92282, respectively and U.S. Publications 2003/0050229 A1 and 2003/0060400 A1. A method for the treatment of HCV and flavivirus and pestivirus infections in humans and other host animals is disclosed that includes administering an effective amount of a biologically active 1', 2', and 3'-branched β-D or β-L nucleosides or a pharmaceutically acceptable salt or prodrug thereof, administered either alone or in combination, optionally in a pharmaceutically acceptable carrier.

International Publication Nos. WO 02/18404 and WO02/100415 to F. Hoffmann-La Roche AG discloses various nucleoside analogs for the treatment of HCV RNA replication.

Pharmasset Limited, in WO 02/32920, discloses various nucleosides for the treatment of a variety of viruses, including Flaviviridae, and in particular HCV.

Merck & Co., Inc. and Isis Pharmaceuticals disclose in International Publication Nos. WO 02/057287 and WO 02/057425 and published U.S. 2002/0147160 A1 various nucleosides, and in particular several pyrrolopyrimidine nucleosides, for the treatment of viruses whose replication is dependent upon RNA-dependent RNA polymerase, including Flaviviridae, and in particular HCV.

In view of the severity of diseases associated with pestiviruses and flaviviruses, and their pervasiveness in animals, including humans, it is an object of the present invention to provide a compound, method and composition for the treatment of a host, including animals and especially humans, infected with flavivirus or pestivirus.

It is a further object to provide a compound, method and composition for the treatment of a host, including animals and especially humans, infected with hepaciviruses.

SUMMARY OF THE INVENTION

It has been found that β-L- or β-D-2',3'-dideoxynucleosides show inhibitory activity against Flaviviridae viruses, and in particular, HCV polymerase. Therefore, a method for the treatment and/or prophylaxis of a Flaviviridae infection, in particular, a HCV infection, in a host, and in particular, a human, is provided that includes administering an effective amount of a β-L- or β-D-2',3'-dideoxynucleoside (alternatively referred to herein as β-L- or β-D-ddN). Uses of an effective amount of a β-L- or β-D-2',3'-dideoxynucleoside for the treatment and/or prophylaxis of and in the manufacture of a medicament for the treatment and/or prophylaxis of a Flaviviridae infection, in particular, a HCV infection, in a host, and in particular, a human, are also provided. Pharmaceutical compositions comprising an effective amount of a β-L- or β-D-2',3'-dideoxynucleoside, are also provided for the treatment and/or prophylaxis of a Flaviviridae infection, in particular, a HCV infection, in a host, and in particular, a human.

In one embodiment of the invention, the active compound is of the formula:

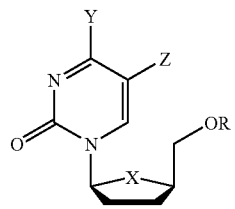

or its pharmaceutically acceptable salt or prodrug thereof, wherein i) X is O, S, S=O, $SO_2$, $NR^1$, $N^+R^1R^2$, $CH_2$, CHF and $CR^3R^4$;
  $R^1$ and $R^2$ are independently hydrogen, $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl, or $C_{3-8}$ ($C_3$, $C_4$, $C_5$, $C_6$, $C_7$, or $C_8$) cycloalkyl;
  $R^3$ and $R^4$ are independently hydrogen, halogen (F, Cl, Br, or I), OH or $OR^5$;
  $R^5$ is hydrogen or a hydroxyl-protecting group, such as alkyl, acyl or silyl;

ii) Y is $NH_2$, $NHR^6$, $NR^6R^7$, OH or $OR^8$
  each $R^6$, $R^7$ and $R^8$ is independently H, $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl, $C_{3-8}$ ($C_3$, $C_4$, $C_5$, $C_6$, $C_7$, or $C_8$) cycloalkyl, cyclopropyl, or $C_{2-6}$ ($C_2$, $C_3$, $C_4$, $C_5$, or $C_6$) acyl;

iii) Z is chosen from hydrogen, halogen (F, Cl, Br, or I), $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl, CN, $CF_3$, $N_3$, $NO_2$, aryl, heteroaryl and $COR^9$;
  $R^9$ is chosen from H, OH, SH, $C_{1-6}$ ($C_1$, $C_2$, $C_3$, $C_4$, $C_5$, or $C_6$) alkyl, $C_{1-6}$ ($C_1$, $C_2$, $C_3$, $C_4$, $C_5$, or $C_6$) aminoalkyl, $C_{1-6}$ ($C_1$, $C_2$, $C_3$, $C_4$, $C_5$, or $C_6$) alkoxy and $C_{1-6}$ ($C_1$, $C_2$, $C_3$, $C_4$, $C_5$, or $C_6$) thioalkyl; and iv) R is hydrogen, phosphate (including mono-, di- or triphosphate and a stabilized phosphate); acyl (including lower acyl); —$C(O)R^{10}$, alkyl (including lower alkyl); sulfonate ester (including alkyl or arylalkyl); sulfonyl (including methanesulfonyl and benzyl, wherein the phenyl group is optionally substituted with one or more substituents as described in the definition of aryl given herein); a lipid (including a phospholipid); an amino acid; a carbohydrate; a peptide; a cholesterol; or other pharmaceutically acceptable leaving group, which, when administered in vivo, is capable of providing a compound wherein R is H or phosphate;
  $R^{10}$ is a $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl, aryl, monophosphate, diphosphate, triphosphate, or —$P(O)(OR^{11})_2$;
  each $R^{11}$ is independently hydrogen, $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl or a hydroxyl-protecting group.

The compound of the present invention can be in the form of the β-L or β-D configuration. In a preferred embodiment, the compound is in the β-L configuration.

In one particular embodiment of the present invention, the active compound is β-L-2',3'-dideoxy-5-substituted-cytidine. In one preferred embodiment, the active compound is β-L-2',3'-dideoxy-5-fluorocytidine (also referred to as β-L-ddFC). In another embodiment, the active compound is β-L-2',3'-dideoxy-cytidine (also referred to as β-L-ddC).

In addition, the β-L- or β-D-2',3'-dideoxynucleosides, and in particular, L-ddFC, are inhibitors of HIV and HBV. Therefore, these compounds can also be used to treat double or triple infection (e.g., HIV and HCV, or HBV and HCV, or HIV, HBV, and HCV).

The present invention provides a method for the treatment and/or prophylaxis of a Flaviviridae viral infection, and in particular a HCV infection, in a host comprising administering a therapeutically effective amount of at least one 2',3'-dideoxynucleoside of the present invention, or its pharmaceutically acceptable salt or prodrug, optionally in a pharmaceutically acceptable carrier or excipient, as described in the present application.

The present invention provides a method for the treatment and/or prophylaxis of a Flaviviridae viral infection, and in particular a HCV infection, in a host comprising administering a therapeutically effective amount of at least one 2',3'-dideoxynucleoside of the present invention, or its pharmaceutically acceptable salt or prodrug, optionally in a pharmaceutically acceptable carrier or excipient, in combination and/or alternation with one or more other antiviral agent(s), as described in the present application.

The present invention provides a method for reducing the biological activity of a Flaviviridae viral infection, and in particular a HCV infection, in a host comprising administering a therapeutically effective amount of at least one 2',3'-dideoxynucleoside of the present invention, or its pharmaceutically acceptable salt or prodrug, optionally in a pharmaceutically acceptable carrier or excipient, as described in the present application.

The present invention provides a method for reducing the biological activity of a Flaviviridae viral infection, and in particular a HCV infection, in a host comprising administering a therapeutically effective amount of at least one 2',3'-dideoxynucleoside of the present invention, or its pharmaceutically acceptable salt or prodrug, optionally in a pharmaceutically acceptable carrier or excipient, in combination and/or alternation with one or more other antiviral agent(s), as described in the present application.

In another aspect, a pharmaceutical composition comprising a 2',3'-dideoxynucleoside of the present invention, or its pharmaceutically acceptable salt or prodrug, together with a pharmaceutically acceptable carrier or excipient is provided.

In another aspect, a pharmaceutical composition comprising a 2',3'-dideoxynucleoside of the present invention, or its pharmaceutically acceptable salt or prodrug together with a pharmaceutically acceptable carrier or excipient, together with one or more other antiviral agent(s) is provided.

In another aspect, a pharmaceutical composition for the treatment and/or prophylaxis of a Flaviviridae viral infection, and in particular a HCV infection, in a host comprising a 2',3'-dideoxynucleoside of the present invention, or its pharmaceutically acceptable salt or prodrug, together with a pharmaceutically acceptable carrier or excipient is provided.

In another aspect, a pharmaceutical composition for the treatment and/or prophylaxis of a Flaviviridae viral infection, and in particular a HCV infection, in a host comprising a 2',3'-dideoxynucleoside of the present invention, or its pharmaceutically acceptable salt or prodrug together with a pharmaceutically acceptable carrier or excipient, together with one or more other antiviral agent(s) is provided.

In another aspect, a pharmaceutical composition for reducing the biological activity of a Flaviviridae viral infection, and in particular a HCV infection, in a host comprising a 2',3'-dideoxynucleoside of the present invention, or its pharmaceutically acceptable salt or prodrug, together with a pharmaceutically acceptable carrier or excipient is provided.

In another aspect, a pharmaceutical composition for reducing the biological activity of a Flaviviridae viral infection, and in particular a HCV infection, in a host comprising a 2',3'-dideoxynucleoside of the present invention, or its pharmaceutically acceptable salt or prodrug together with a pharmaceutically acceptable carrier or excipient, together with one or more other antiviral agent(s) is provided.

The present invention provides a use of a 2',3'-dideoxynucleoside of the present invention, or its pharmaceutically acceptable salt or prodrug, optionally in a pharmaceutically acceptable carrier or excipient, for the treatment and/or prophylaxis of a Flaviviridae viral infection, and in particular a HCV infection, in a host as described in the present application.

The present invention provides a use of a 2',3'-dideoxynucleoside of the present invention, or its pharmaceutically acceptable salt or prodrug, optionally in a pharmaceutically acceptable carrier or excipient, for the treatment and/or prophylaxis of a Flaviviridae viral infection, and in particular a HCV infection, in a host in combination and/or alternation with one or more other antiviral agent(s), as described in the present application.

The present invention provides a use of a 2',3'-dideoxynucleoside of the present invention, or its pharmaceutically acceptable salt or prodrug, optionally in a pharmaceutically acceptable carrier or excipient, for reducing the biological activity of a Flaviviridae viral infection, and in particular a HCV infection, in a host as described in the present application.

The present invention provides a use of a 2',3'-dideoxynucleoside of the present invention, or its pharmaceutically acceptable salt or prodrug, optionally in a pharmaceutically acceptable carrier or excipient, for reducing the biological activity of a Flaviviridae viral infection, and in particular a HCV infection, in a host in combination and/or alternation with one or more other antiviral agent(s), as described in the present application.

The present invention provides a use of a 2',3'-dideoxynucleoside of the present invention, or its pharmaceutically acceptable salt or prodrug, optionally in a pharmaceutically acceptable carrier or excipient, in the manufacture of a medicament for the treatment and/or prophylaxis of a Flaviviridae viral infection, and in particular a HCV infection, in a host as described in the present application.

The present invention provides a use of a 2',3'-dideoxynucleoside of the present invention, or its pharmaceutically acceptable salt or prodrug, optionally in a pharmaceutically acceptable carrier or excipient, in a host in combination and/or alternation with one or more other antiviral agent(s), in the manufacture of a medicament for the treatment and/or prophylaxis of a Flaviviridae viral infection, and in particular a HCV infection, in a host as described in the present application.

The present invention provides a use of the 2',3'-dideoxynucleoside of the present invention, or its pharmaceutically acceptable salt or prodrug, optionally in a pharmaceutically acceptable carrier or excipient, in the manufacture of a medicament for reducing the biological activity of a Flaviviridae viral infection, and in particular a HCV infection, in a host, as described in the present application.

The present invention provides a use of the 2',3'-dideoxynucleoside of the present invention, or its pharmaceutically acceptable salt or prodrug, optionally in a pharmaceutically acceptable carrier or excipient, in a host in combination and/or alternation with one or more other antiviral agent(s), in the manufacture of a medicament for reducing the biological activity of a Flaviviridae viral infection, and in particular a HCV infection, in a host as described in the present application.

BRIEF DESCRIPTION OF THE FIGURES

FIG. 1 is a non-limiting example of the synthesis of active compounds of the present invention, and in particular, the synthesis of β-L-2',3'-dideoxylnucleosides and their triphosphate derivatives.

FIG. 2 is an illustration of the dose-dependent inhibition of NS5B enzyme with β-L-ddFC triphosphate (also referred to as β-L-ddFC-TP).

FIG. 3 is a graphical representation of the dose-dependent inhibition of NS5B enzyme with β-L-ddFC triphosphate (also referred to as β-L-ddFC-TP).

FIG. 4 is a graphical representation of the dose-dependent inhibition when treated with L-ddFC, but shows no inhibition when treated with L-ddC.

FIG. 5 is a graphical representation of the dependent increase of inhibition of L-ddFC with the increase in manganese concentration. The activity of L-ddC is not affected by concentrations of manganese.

DETAILED DESCRIPTION OF THE INVENTION

It was found in the present invention that β-L- or β-D-2',3'-dideoxynucleosides show inhibitory activity against Flaviviridae viruses, and in particular, HCV polymerase. Therefore, a method for the treatment or prevention of a host, and in particular, a human, infected with Flaviviridae viruses, in particular, hepatitis C virus (HCV), is provided that includes administering an effective amount of a β-L- or β-D-2',3'-dideoxynucleoside (alternatively referred to herein as β-L- or β-D-ddN).

The β-L- or β-D-2',3'-dideoxynucleosides of the present invention may also be inhibitors of HIV and/or HBV. Therefore, these compounds may also be used to treat dual or triple infection (e.g., HIV and HCV, or HBV and HCV, or HIV, HBV and HCV).

In one embodiment, the Flaviviridae viral infection is chosen from hepatitis C virus (HCV), bovine viral diarrhea virus (BVDV), hog cholera and yellow fever. In another embodiment, the Flaviviridae viral infection is HCV.

The present invention provides a method for the treatment or prophylaxis of a Flaviviridae viral infection, and in particular a HCV infection, in a host comprising administering a therapeutically effective amount of at least one 2',3'-dideoxynucleoside of the present invention, or its pharmaceutically acceptable salt or prodrug, optionally in a pharmaceutically acceptable carrier or excipient, as described in the present application.

The present invention provides a method for the treatment or prophylaxis of a Flaviviridae viral infection, and in particular a HCV infection, in a host comprising administering a therapeutically effective amount of at least one 2',3'-dideoxynucleoside of the present invention, or its pharmaceutically acceptable salt or prodrug, optionally in a pharmaceutically acceptable carrier or excipient, in combination or alternation with one or more other antiviral agent(s), as described in the present application.

The present invention provides a method for reducing the biological activity of a Flaviviridae viral infection, and in particular a HCV infection, in a host comprising administering a therapeutically effective amount of at least one 2',3'-dideoxynucleoside of the present invention, or its pharmaceutically acceptable salt or prodrug, optionally in a pharmaceutically acceptable carrier or excipient, as described in the present application.

The present invention provides a method for reducing the biological activity of a Flaviviridae viral infection, and in particular a HCV infection, in a host comprising administering a therapeutically effective amount of at least one 2',3'-dideoxynucleoside of the present invention, or its pharmaceutically acceptable salt or prodrug, optionally in a pharmaceutically acceptable carrier or excipient, in combination or alternation with one or more other antiviral agent(s), as described in the present application.

In another aspect, a pharmaceutical formulation comprising the 2',3'-dideoxynucleoside of the present invention, or its pharmaceutically acceptable salt or prodrug together with a pharmaceutically acceptable carrier or excipient is provided.

In another aspect, a pharmaceutical formulation comprising the 2',3'-dideoxynucleoside of the present invention, or its pharmaceutically acceptable salt or prodrug together with a pharmaceutically acceptable carrier or excipient, together with one or more other antiviral agent(s) is provided.

The present invention provides a use of the 2',3'-dideoxynucleoside of the present invention, or its pharmaceutically acceptable salt or prodrug, optionally in a pharmaceutically acceptable carrier or excipient, for the treatment or prophylaxis of a Flaviviridae viral infection, and in particular a HCV infection, in a host as described in the present application.

The present invention provides a use of the 2',3'-dideoxynucleoside of the present invention, or its pharmaceutically acceptable salt or prodrug, optionally in a pharmaceutically acceptable carrier or excipient, for the treatment or prophylaxis of a Flaviviridae viral infection, and in particular a HCV infection, in a host in combination or alternation with one or more other antiviral agent(s), as described in the present application.

The present invention provides a use of the 2',3'-dideoxynucleoside of the present invention, or its pharmaceutically acceptable salt or prodrug, optionally in a pharmaceutically acceptable carrier or excipient, in the manufacture of a medicament for the treatment or prophylaxis of a Flaviviridae viral infection, and in particular a HCV infection, in a host as described in the present application.

The present invention provides a use of the 2',3'-dideoxynucleoside of the present invention, or its pharmaceutically acceptable salt or prodrug, optionally in a pharmaceutically acceptable carrier or excipient, together with another antiviral agent in the manufacture of a medicament for the treatment or prophylaxis of a Flaviviridae viral infection, and in particular a HCV infection, in a host as described in the present application.

I. ACTIVE COMPOUND

In one embodiment of the invention, the active compound is of the formula:

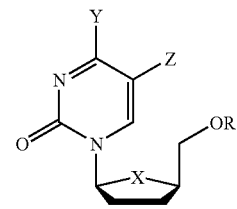

or a pharmaceutically acceptable salt or prodrug thereof, wherein v) X is O, S, S=O, $SO_2$, $NR^1$, $N^+R^1R^2$, $CH_2$, CHF and $CR^3R^4$;

$R^1$ and $R^2$ are independently hydrogen, $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl, or $C_{3-8}$ ($C_3$, $C_4$, $C_5$, $C_6$, $C_7$, or $C_8$) cycloalkyl;

$R^3$ and $R^4$ are independently hydrogen, halogen (F, Cl, Br, or I), OH or $OR^5$;

$R^5$ is hydrogen or a hydroxyl-protecting group, such as alkyl, acyl or silyl;

vi) Y is $NH_2$, $NHR^6$, $NR^6R^7$, OH or $OR^8$ each $R^6$, $R^7$ and $R^8$ is independently H, $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl, $C_{3-8}$ ($C_3$, $C_4$, $C_5$, $C_6$, $C_7$, or $C_8$) cycloalkyl, cyclopropyl, or $C_{2-6}$ ($C_2$, $C_3$, $C_4$, $C_5$, or $C_6$) acyl;

vii) Z is chosen from hydrogen, halogen (F, Cl, Br, or I), $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl, CN, $CF_3$, $N_3$, $NO_2$, aryl, heteroaryl and $COR^9$;

$R^9$ is chosen from H, OH, SH, $C_{1-6}$ ($C_1$, $C_2$, $C_3$, $C_4$, $C_5$, or $C_6$) alkyl, $C_{1-6}$ ($C_1$, $C_2$, $C_3$, $C_4$, $C_5$, or $C_6$) aminoalkyl, $C_{1-6}$ ($C_1$, $C_2$, $C_3$, $C_4$, $C_5$, or $C_6$) alkoxy and $C_{1-6}$ ($C_1$, $C_2$, $C_3$, $C_4$, $C_5$, or $C_6$) thioalkyl; and viii) R is hydrogen, phosphate (including mono-, di- or triphosphate and a stabilized phosphate); acyl (including lower acyl); —C(O)$R^{10}$, alkyl (including lower alkyl); sulfonate ester (including alkyl or arylalkyl); sulfonyl (including methanesulfonyl and benzyl, wherein the phenyl group is optionally substituted with one or more substituents as described in the definition of aryl given herein); a lipid (including a phospholipid); an amino acid; a carbohydrate; a peptide; a cholesterol; or other pharmaceutically acceptable leaving group, which, when administered in vivo, is capable of providing a compound wherein R is H or phosphate;

$R^{10}$ is a $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl, aryl, monophosphate, diphosphate, triphosphate, or —P(O)(OR$^{11}$)$_2$;

each $R^{11}$ is independently hydrogen, $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl or a hydroxyl-protecting group.

The active compound of the present invention can be in the form of the β-L or β-D configuration. In a preferred embodiment, the compound is in the β-L configuration. In one embodiment of the invention, the 2',3'-dideoxynucleoside of the present invention is a racemic mixture. In one embodiment of the invention, the 2',3'-dideoxynucleoside of the present invention is in an enantiomerically pure form of the desired enantiomer (at least 95% pure or greater, and preferably at least 98 or 99% pure). In another embodiment of the invention, the desired 2',3'-dideoxynucleoside enantiomer of the present invention is substantially free of the undesired enantiomer. In another embodiment of the invention, the desired 2',3'-dideoxynucleoside enantiomer of the present invention is in an isolated form.

In one preferred embodiment, the active compound is β-L-2',3'-dideoxy-5-fluorocytidine (also referred to as β-L-ddFC), of the structure:

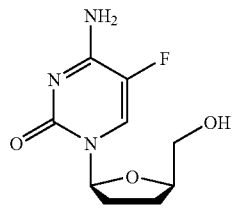

or a pharmaceutically acceptable salt or prodrug thereof.

In another preferred embodiment, the active compound is β-L-2',3'-dideoxy-5-fluorocytidine, of the structure:

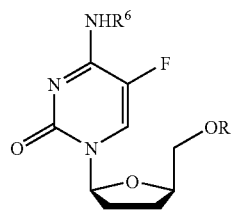

or a pharmaceutically acceptable salt thereof, wherein R and $R^6$ are as defined above.

In one embodiment, the active compound is β-L-2',3'-dideoxy-5-fluorocytidine triphosphate (also referred to as β-L-ddFC-TP), of the structure:

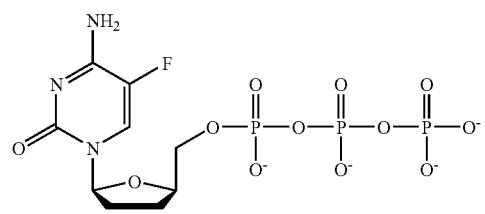

or a pharmaceutically acceptable salt or prodrug thereof.

In an alternate embodiment, the active compound is β-L-2',3'-dideoxy-5-substituted-cytidine, of the structure:

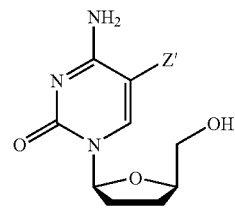

or a pharmaceutically acceptable salt or prodrug thereof, wherein

Z' is chosen from halogen (F, Cl, Br, or I), $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl, CN, CF$_3$, N$_3$, NO$_2$, aryl, heteroaryl and COR$^9$; and $R^9$ is chosen from H, OH, SH, $C_{1-6}$ ($C_1$, $C_2$, $C_3$, $C_4$, $C_5$, or $C_6$) alkyl, $C_{1-6}$ ($C_1$, $C_2$, $C_3$, $C_4$, $C_5$, or $C_6$) aminoalkyl, $C_{1-6}$ ($C_1$, $C_2$, $C_3$, $C_4$, $C_5$, or $C_6$) alkoxy and $C_{1-6}$ ($C_1$, $C_2$, $C_3$, $C_4$, $C_5$, or $C_6$) thioalkyl.

In an alternate embodiment, the active compound is β-L-2',3'-dideoxy-5-substituted-cytidine, of the structure:

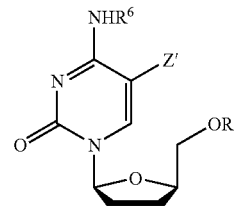

or a pharmaceutically acceptable salt thereof, wherein
  (i) $R^6$ is H, $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl, $C_{3-8}$ ($C_3$, $C_4$, $C_5$, $C_6$, $C_7$, or $C_8$) cycloalkyl, cyclopropyl, or $C_{2-6}$ ($C_2$, $C_3$, $C_4$, $C_5$, or $C_6$) acyl; and
  (ii) R is hydrogen, phosphate (including mono-, di- or triphosphate and a stabilized phosphate); acyl (including lower acyl); —C(O)R$^{10}$, alkyl (including lower alkyl); sulfonate ester (including alkyl or arylalkyl); sulfonyl (including methanesulfonyl and benzyl, wherein the phenyl group is optionally substituted with one or more substituents as described in the definition of aryl given herein); a lipid (including a phospholipid); an amino acid; a carbohydrate; a peptide; a cholesterol; or other pharmaceutically acceptable leaving group, which, when administered in vivo, is capable of providing a compound wherein R is H or phosphate;
  (iii) Z' is chosen from halogen (F, Cl, Br, or I), $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl, CN, CF$_3$, N$_3$, NO$_2$, aryl, heteroaryl and COR$^9$; and
  $R^9$ is chosen from H, OH, SH, $C_{1-6}$ ($C_1$, $C_2$, $C_3$, $C_4$, $C_5$, or $C_6$) alkyl, $C_{1-6}$ ($C_1$, $C_2$, $C_3$, $C_4$, $C_5$, or $C_6$) aminoalkyl, $C_{1-6}$ ($C_1$, $C_2$, $C_3$, $C_4$, $C_5$, or $C_6$) alkoxy and $C_{1-6}$ ($C_1$, $C_2$, $C_3$, $C_4$, $C_5$, or $C_6$) thioalkyl;

optionally in a pharmaceutically acceptable carrier.

In another embodiment, the active compound is β-L-2',3'-dideoxy-5-substituted-cytidine triphosphate, of the structure:

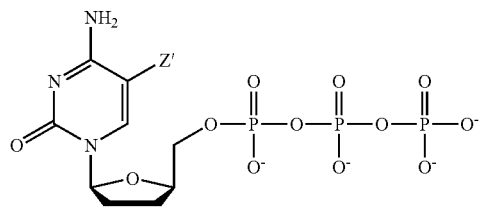

or a pharmaceutically acceptable salt or prodrug thereof; wherein

Z is chosen from halogen (F, Cl, Br, or I), $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl, CN, $CF_3$, $N_3$, $NO_2$, aryl, heteroaryl and $COR^9$; and $R^9$ is chosen from H, OH, SH, $C_{1-6}$ ($C_1$, $C_2$, $C_3$, $C_4$, $C_5$, or $C_6$) alkyl, $C_{1-6}$ ($C_1$, $C_2$, $C_3$, $C_4$, $C_5$, or $C_6$) aminoalkyl, $C_{1-6}$ ($C_1$, $C_2$, $C_3$, $C_4$, $C_5$, or $C_6$) alkoxy and $C_{1-6}$ ($C_1$, $C_2$, $C_3$, $C_4$, $C_5$, or $C_6$) thioalkyl.

Stereochemistry

The nucleosides formed from these coupling reactions may have asymmetric centers and occur as racemates, racemic mixtures, individual diastereomers or enantiomers, with all isomeric forms being included in the present invention. Nucleosides having a chiral center may exist in and be isolated in optically active and racemic forms. Some compounds may exhibit polymorphism. The nucleosides formed from the coupling reaction can encompasses racemic, optically-active, polymorphic, or stereoisomeric form, or mixtures thereof, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution.

Optically active forms of the compounds can be prepared using any method known in the art, including by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including simulated moving bed chromatography, is used in one embodiment. A wide variety of chiral stationary phases are commercially available.

II. DEFINITIONS

As used herein, the term "enantiomerically pure" refers to a nucleoside composition that comprises at least approximately 95% by weight, and preferably approximately 97%, 98%, 99% or 100% of a single enantiomer of that nucleoside.

As used herein, the term "substantially free of" or "substantially in the absence of" refers to a nucleoside composition that includes at least preferably 95 to 98% by weight, and even more preferably 99 to 100% by weight, of the designated enantiomer of that nucleoside.

Similarly, the term "isolated" refers to a nucleoside composition that includes at least 85 or 90% by weight, preferably 95 to 98% by weight, and even more preferably 99 to 100% by weight, of the nucleoside, the remainder comprising other chemical species or enantiomers.

The term "alkyl," as used herein, unless otherwise specified, refers to a saturated straight, branched, or cyclic, primary, secondary, or tertiary hydrocarbon of typically $C_1$ to $C_{10}$, and specifically includes methyl, $CF_3$, $CCl_3$, $CFCl_2$, $CF_2Cl$, ethyl, $CH_2CF_3$, $CF_2CF_3$, propyl, isopropyl, cyclopropyl, butyl, isobutyl, t-butyl, cyclobutyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. When the terms $C_{1-6}$ ($C_1$, $C_2$, $C_3$, $C_4$, $C_5$, or $C_6$) alkyl, $C_{2-6}$ ($C_2$, $C_3$, $C_4$, $C_5$, or $C_6$) alkenyl, $C_{2-6}$ ($C_2$, $C_3$, $C_4$, $C_5$, or $C_6$) alkynyl, $C_{3-8}$ ($C_3$, $C_4$, $C_5$, $C_6$, $C_7$, or $C_8$) cycloalkyl or the like are used in the text, they are intended to refer specifically to each compound that falls within the referenced class. As an illustrative example, $C_{1-6}$ ($C_1$, $C_2$, $C_3$, $C_4$, $C_5$, or $C_6$) alkyl includes individually every alkyl moiety with one to six carbon atoms, including those set out in this definition of alkyl. The term includes both substituted and unsubstituted alkyl groups. The alkyl group can be optionally substituted with one or more moieties selected from the group consisting of halo (F, Cl, Br, or I), haloalkyl, hydroxyl, carboxyl, acyl, acyloxy, amino, amido, carboxyl derivatives, alkylamino, dialkylamino, arylamino, alkoxy, aryloxy, nitro, cyano, azido, thiol, imine, sulfonic acid, sulfate, sulfonyl, sulfanyl, sulfinyl, sulfamoyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene et al, *Protective Groups in Organic Synthesis*, John Wiley & Sons, Second Edition, 1991, incorporated by reference.

The term "aryl," alone or in combination, means a carbocyclic aromatic system containing one, two or three rings wherein such rings may be attached together in a pendent manner or may be fused. The "aryl" group can be optionally substituted with one or more of the moieties selected from the group consisting of alkyl, alkenyl, alkynyl, heteroaryl, heterocyclic, carbocyclic, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, halogen (F, Cl, Br, or I), haloalkylthio, haloalkoxy, haloalkyl, hydroxyl, carboxyl, acyl, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that does not inhibit the pharmacological activity of this compound, either unprotected, or protected as necessary, as known to those skilled in the art, for example, as taught in Greene et al., "Protective Groups in Organic Synthesis," John Wiley & Sons, Second Edition, 1999. In addition, adjacent groups on an "aryl" ring may combine to form a 5- to 7-membered saturated or partially unsaturated carbocyclic, aryl, heteroaryl or heterocyclic ring, which in turn may be substituted as above.

The heteroaryl ring may optionally be substituted by one or more substituent listed as optional substituents for aryl. In addition, adjacent groups on the heteroaryl or heterocyclic ring may combine to form a 5- to 7-membered carbocyclic, aryl, heteroaryl or heterocyclic ring, which in turn may be substituted as above. Nonlimiting examples of heterocylics and heteroaromatics are pyrrolidinyl, tetrahydrofuryl, tetrahydrofuranyl, pyranyl, purinyl, tetrahydropyranyl, piperazinyl, piperidinyl, morpholino, thiomorpholino, tetrahydropyranyl, imidazolyl, pyrrolinyl, pyrazolinyl, indolinyl, dioxolanyl, or 1,4-dioxanyl, aziridinyl, furyl, furanyl, pyridyl, pyridinyl, pyridazinyl, pyrimidinyl, benzoxazolyl, 1,2,4-oxadiazolyl, 1,3,4-oxadiazolyl, 1,3,4-thiadiazole, indazolyl, triazinayl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isooxazolyl, 1,2,4-oxadiazolyl, 1,3,4-oxadiazolyl, pyrrolyl, quinazolinyl, quinoxalinyl, benzoxazolyl, quinolinyl, isoquinolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, triazolopyridinyl or pteridinyl wherein said heteroaryl or heterocyclic group can be optionally substituted with one or more substituent selected from the same substituents as set out above for aryl groups. Functional oxygen and nitrogen groups on the heteroaryl group can be protected as necessary or desired. Suitable protecting groups can include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl.

The term "lower alkyl," as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred.

The term "alkenyl," alone or in combination, means a moiety having one or more double carbon-carbon bonds, including but not limited to ethenyl and propenyl The term "alkynyl," alone or in combination means a moiety having one or more triple carbon-carbon bonds, including but not limited to ethynyl and propynyl.

The terms "alkylamino" or "arylamino" refer to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen (F, Cl, Br, or I), $C_1$ to $C_4$ alkyl or $C_1$ to $C_4$ alkoxy, sulfonate esters such as alkyl or aralkyl sulfonyl including methanesulfonyl, the mono-, di- or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term "amino acid" includes naturally occurring and synthetic α, β, γ, or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

The term "host," as used herein, refers to a unicellular or multicellular organism in which the virus can replicate, including cell lines and animals, and preferably a human. Alternatively, the host can be carrying a part of the viral genome, whose replication or function can be altered by the compounds of the present invention. The term host specifically refers to infected cells, cells transfected with all or part of the viral genome and animals, in particular, primates (including chimpanzees) and humans. In most animal applications of the present invention, the host is a human patient. Veterinary applications, in certain indications, however, are clearly anticipated by the present invention (such as chimpanzees).

III. NUCLEOTIDE SALT OR PRODRUG FORMULATIONS

The term "pharmaceutically acceptable salt or prodrug" is used throughout the specification to describe any pharmaceutically acceptable form (such as an ester, phosphate ester, salt of an ester or another derivative) of a nucleoside compound which, upon administration to a patient, provides the specified nucleoside compound in active form. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. Typical examples of prodrugs include compounds that have biologically labile protecting groups on a functional moiety of the active compound. The compounds of this invention possess antiviral activity against Flaviviridae, or are metabolized to a compound that exhibits such activity.

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartrate, succinate, benzoate, ascorbate, α-ketoglutarate and α-glycerophosphate. Suitable inorganic salts may also be formed, including, sulfate, nitrate, bicarbonate and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

Any of the nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono-, di- or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones & N. Bischofberger, *Antiviral Research*, 27 (1995) 1-17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera L. S., Iyer N, Leake E., Raben A., Modest E. K., Daniel L. W., and C. Piantadosi, "Novel membrane-interactive ether lipid analogs that inhibit infectious HIV-1 production and induce defective virus formation," *AIDS Res. Hum. Retroviruses*, 1990, 6, 491-501; Piantadosi C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi & E. J. Modest, "Synthesis and evaluation of novel ether lipid nucleoside conjugates for anti-HIV activity," *J. Med. Chem.*, 1991, 34, 1408-1414; Hostetler K. Y., D. D. Richman, D. A. Carson, L. M. Stuhmiller, G. M. T. van Wijk, and H. van den Bosch, "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine," *Antimicrob. Agents Chemother.*, 1992, 36, 2025-2029; Hostetler, K. Y., L. M. Stuhmiller, H. B. Lenting, H. van den Bosch, and D. D. Richman, "Synthesis and antiretroviral activity of phospholipid analogs of azidothymidine and other antiviral nucleosides." *J. Biol. Chem.*, 1990, 265, 61127.

Nonlimiting examples of US patents that disclose suitable lipophilic substituents that can be covalently incorporated into the nucleoside, preferably at the 5'-OH position of the nucleoside or lipophilic preparations, include U.S. Pat. Nos. 5,149,794 (1992, Yatvin et al.); 5,194,654 (Hostetler et al.), 5,223,263 (1993, Hostetler et al.); 5,256,641 (1993, Yatvin et al.); 5,411,947 (1995, Hostetler et al.); 5,463,092 (1995, Hostetler et al.); 5,543,389 (1996, Yatvin et al.); 5,543,390 (1996, Yatvin et al.); 5,543,391 (1996, Yatvin et al.); and 5,554,728 (1996; Basava et al.), all of which are incorporated by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721, all of which are incorporated by reference. The compounds can also be provided as "SATE" derivatives.

Prodrugs also include amino acid esters of the disclosed nucleosides (see, e.g., European Patent Specification No. 99493, the text of which is incorporated by reference, which describes amino acid esters of acyclovir, specifically the glycine and alanine esters which show improved water-solubility compared with acyclovir itself, and U.S. Pat. No. 4,957,924 (Beauchamp), which discloses the valine ester of acyclovir, characterised by side-chain branching adjacent to the α-carbon atom, which showed improved bioavailability after oral administration compared with the alanine and glycine esters). A process for preparing such amino acid esters is disclosed in U.S. Pat. No. 4,957,924 (Beauchamp), which is incorporated by reference. As an alternative to the use of valine itself, a functional equivalent of the amino acid may be used (e.g., an acid halide such as the acid chloride, or an acid anhydride). In such a case, to avoid undesirable side-reactions, it may be is advantageous to use an amino-protected derivative.

IV. COMBINATION OR ALTERNATION THERAPY

It has been recognized that drug-resistant variants of Flaviviridae can emerge after prolonged treatment with an antiviral agent. Drug resistance most typically occurs by mutation of a gene that encodes for an enzyme used in viral replication. The efficacy of a drug against a Flaviviridae infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Nonlimiting examples of antiviral agents that can be used in combination and/or alternation with the compounds disclosed herein include:

(1) Protease Inhibitors

Non-limiting examples include substrate-based NS3 protease inhibitors (Attwood et al., Antiviral peptide derivatives, PCT WO 98/22496, 1998; Attwood et al., Antiviral Chemistry and Chemotherapy 1999, 10, 259-273; Attwood et al., Preparation and use of amino acid derivatives as anti-viral agents, German Patent Pub. DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, *Hepatitis C inhibitor peptide analogues*, PCT WO 99/07734); Non-substrate-based NS3 protease inhibitors such as 2,4,6-trihydroxy-3-nitro-benzamide derivatives (Sudo K. et al., *Biochemical and Biophysical Research Communications*, 1997, 238, 643-647; Sudo K. et al. *Antiviral Chemistry and Chemotherapy*, 1998, 9, 186), including RD3-4082 and RD3-4078, the former substituted on the amide with a 14 carbon chain and the latter processing a para-phenoxyphenyl group; and Sch 68631, a phenanthrenequinone, an HCV protease inhibitor (Chu M. et al., *Tetrahedron Letters* 37:7229-7232, 1996).

Sch 351633, isolated from the fungus *Penicillium griseofulvum*, was identified as a protease inhibitor (Chu M. et al., *Bioorganic and Medicinal Chemistry Letters* 9:1949-1952). Eglin c, isolated from leech, is a potent inhibitor of several serine proteases such as *S. griseus* proteases A and B, α-chymotrypsin, chymase and subtilisin. Qasim M. A. et al., *Biochemistry* 36:1598-1607, 1997.

U.S. patents disclosing protease inhibitors for the treatment of HCV include, for example, U.S. Pat. No. 6,004,933 to Spruce et al. which discloses a class of cysteine protease inhibitors for inhibiting HCV endopeptidase 2; U.S. Pat. No. 5,990,276 to Zhang et al. which discloses synthetic inhibitors of hepatitis C virus NS3 protease; U.S. Pat. No. 5,538,865 to Reyes et a; WO 02/008251 to Corvas International, Inc, and WO 02/08187 and WO 02/008256 to Schering Corporation. HCV inhibitor tripeptides are disclosed in U.S. Pat. Nos. 6,534,523, 6,410,531, and 6,420,380 to Boehringer Ingelheim and WO 02/060926 to Bristol Myers Squibb. Diaryl peptides as NS3 serine protease inhibitors of HCV are disclosed in WO 02/48172 to Schering Corporation. Imidazolidindiones as NS3 serine protease inhibitors of HCV are disclosed in WO 02/08198 to Schering Corporation and WO 02/48157 to Bristol Myers Squibb. WO 98/17679 to Vertex Pharmaceuticals and WO 02/48116 to Bristol Myers Squibb also disclose HCV protease inhibitors.

(2) Thiazolidine derivatives (non-limiting examples include those which show relevant inhibition in a reverse-phase HPLC assay with an NS3/4A fusion protein and NS5A/5B substrate (Sudo K. et al., *Antiviral Research*, 1996, 32, 9-18), especially compound RD-1-6250, possessing a fused cinnamoyl moiety substituted with a long alkyl chain, RD4 6205 and RD4 6193);

(3) Thiazolidines and benzanilides (non-limiting examples include those identified in Kakiuchi N. et al. *J. EBS Letters* 421, 217-220; Takeshita N. et al. *Analytical Biochemistry*, 1997, 247, 242-246);

(4) Phenan-threnequinone (non-limiting examples include those possessing activity against protease in a SDS-PAGE and autoradiography assay isolated from the fermentation culture broth of *Streptomyces* sp., Sch 68631 (Chu M. et al., *Tetrahedron Letters*, 1996, 37, 7229-7232), and Sch 351633, isolated from the fungus *Penicillium griseofulvum*, which demonstrates activity in a scintillation proximity assay (Chu M. et al., *Bioorganic and Medicinal Chemistry Letters* 9, 1949-1952));

(5) Helicase inhibitors (non-limiting examples include those identified in Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

(6) Nucleotide polymerase inhibitors and gliotoxin (non-limiting examples include those identified in Ferrari R. et al. *Journal of Virology*, 1999, 73, 1649-1654, and the natural product cerulenin (Lohmann V. et al., *Virology*, 1998, 249, 108-118));

(7) Antisense phosphorothioate oligodeoxynucleotides (S-ODN) (non-limiting examples include those which are complementary to sequence stretches in the 5' non-coding region (NCR) of the virus (Alt M. et al., *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 1999, 181, 251-257));

(8) Inhibitors of IRES-dependent translation (non-limiting examples include those identified in Ikeda N et al., Agent for the prevention and treatment of hepatitis C, Japanese Patent Pub. JP-08268890; Kai Y. et al. Prevention and treatment of viral diseases, Japanese Patent Pub. JP-10101591);

(9) Ribozymes (non-limiting examples include nuclease-resistant ribozymes (Maccjak, D. J. et al., *Hepatology* 1999, 30, abstract 995) and those disclosed in U.S. Pat. No. 6,043,077 to Barber et al., and U.S. Pat. Nos. 5,869,253 and 5,610,054 to Draper et al.); and

(10) Nucleoside analogs.

(11) Any of the compounds described by Idenix Pharmaceuticals in International Publication Nos. WO 01/90121 and WO 01/92282;

(12) Other patent applications disclosing the use of certain nucleoside analogs to treat hepatitis C virus include: PCT/CA00/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002) and PCT/US02/03086 (WO 02/057287; filed Jan. 18, 2002) filed by Merck & Co., Inc., PCT/EP01/09633 (WO 02/18404; published Aug. 21, 2001) filed by Roche, and PCT Publication Nos. WO 01/79246 (filed Apr. 13, 2001), WO 02/32920 (filed Oct. 18, 2001) and WO 02/48165 by Pharmasset, Ltd.

(13) PCT Publication No. WO 99/43691 to Emory University, entitled "2'-Fluoronucleosides" discloses the use of certain 2'-fluoronucleosides to treat HCV.

(14) Other miscellaneous compounds (including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.)), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056,961), and piperadines (U.S. Pat. No. 5,830,905 to Diana et al.).

Any other compound currently in preclinical or clinical development for treatment of hepatitis C virus including: Interleukin-10 by Schering-Plough, IP-501 by Interneuron, Merimebodib (VX-497) by Vertex, AMANTADINE® (Symmetrel) by Endo Labs Solvay, HEPTAZYME® by RPI, IDN-6556 by Idun Pharma., XTL-002 by XTL., HCV/MF59 by Chiron, CIVACIR (Hepatitis C Immune Globulin) by NABI, LEVOVIRIN® by ICN/Ribapharm, VIRAMIDINE® by ICN/Ribapharm, ZADAXIN® (thymosin alpha-1) by Sci Clone, thymosin plus pegylated interferon by Sci Clone, CEPLENE® (histamine dihydrochloride) by Maxim, VX 950/LY 570310 by Vertex/Eli Lilly, ISIS 14803 by Isis Pharmaceutical/Elan, IDN-6556 by Idun Pharmaceuticals, Inc., JTK 003 by AKROS Pharma, BILN-2061 by Boehringer Ingelheim, CellCept (mycophenolate mofetil) by Roche, T67, a β-tubulin inhibitor, by Tularik, a therapeutic vaccine directed to E2 by Innogenetics, FK788 by Fujisawa Healthcare, Inc., 1 dB 1016 (Siliphos, oral silybin-phosphatdylcholine phytosome), RNA replication inhibitors (VP50406) by ViroPharma/Wyeth, therapeutic vaccine by Intercell, therapeutic vaccine by Epimmune/Genencor, IRES inhibitor by Anadys, ANA 245 and ANA 246 by Anadys, immunotherapy (Therapore) by Avant, protease inhibitor by Corvas/SChering, helicase inhibitor by Vertex, fusion inhibitor by Trimeris, T cell therapy by CellExSys, polymerase inhibitor by Biocryst, targeted RNA chemistry by PTC Therapeutics, Dication by Immtech, Int., protease inhibitor by Agouron, protease inhibitor by Chiron/Medivir, antisense therapy by AVI BioPharma, antisense therapy by Hybridon, hemopurifier by Aethlon Medical, therapeutic vaccine by Merix, protease inhibitor by Bristol-Myers Squibb/Axys, Chron-VacC, a therapeutic vaccine, by Tripep, UT 231B by United Therapeutics, protease, helicase and polymerase inhibitors by Genelabs Technologies, IRES inhibitors by Immusol, R803 by Rigel Pharmaceuticals, INFERGEN® (interferon alphacon-1) by InterMune, OMNIFERON® (natural interferon) by Viragen, ALBUFERON® by Human Genome Sciences, REBIF (interferon beta-1a) by Ares-Serono, Omega Interferon by BioMedicine, Oral Interferon Alpha by Amarillo Biosciences, interferon gamma, interferon tau, and Interferon gamma-1b by InterMune.

In one embodiment, the compounds of the invention may be employed together with at least one other antiviral agent chosen from protease inhibitors, fusion inhibitors, polymerase inhibitors and helicase inhibitors.

In addition, compounds according to the present invention can be administered in combination or alternation with one or more anti-retrovirus, anti-HBV, anti-HCV or anti-Herpetic agent or interferon, anti-cancer or antibacterial agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

V. PHARMACEUTICAL COMPOSITIONS

Pharmaceutical compositions can be prepared that include the above-described compound or its salt or prodrug in a therapeutically effective amount for treating a Flaviviridae infection, optionally in combination with a pharmaceutically acceptable additive, carrier or excipient. A host, including humans, infected with a Flaviviridae virus, or a gene fragment thereof, can be treated by administering to the patient an effective amount of the active compound or a pharmaceutically acceptable prodrug or salt thereof in the presence of a pharmaceutically acceptable carrier or diluent. The therapeutically effective amount may vary with the infection or condition to be treated, its severity, the treatment regimen to be employed, the pharmacokinetics of the agent used, as well as the patient treated. The active materials can be administered by any appropriate route.

In general, it is preferable to administer the pharmaceutical composition in an orally administrable form, but formulations may be administered via parenteral, intravenous, intramuscular, transdermal, buccal, subcutaneous, suppository, or topical administration, among other routes of administration. Enteric-coated oral tablets may also be used to enhance bioavailability and stability of the compounds from an oral route of administration. Intravenous and intramuscular formulations are preferably administered in sterile saline. One of ordinary skill in the art may modify the formulation within the teachings of the specification to provide numerous formulations for a particular route of administration without rendering the compositions of the present invention unstable or compromising its therapeutic activity. In particular, a modification of a desired compound to render it more soluble in water or other vehicle, for example, may be easily accomplished by routine modification (salt formulation, esterification, etc.). Administration of the active compound may range from continuous (intravenous drip) to several oral administrations per day (for example, Q.I.D., B.I.D., etc.).

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred dose of the compound for a Flaviviridae infection will be in the range from about 1 to 50 mg/kg, preferably 1 to 20 mg/kg, of body weight per day, more generally 0.1 to about 100 mg per kilogram body weight of the recipient per day or more, depending upon the compound used, the condition or infection treated and the route of administration. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art. For purposes of the present invention, a prophylactically or preventively effective amount of the compositions, according to the present invention, falls within the same concentration range as set forth above for therapeutically effective amount and is usually the same as a therapeutically effective amount.

The compound is conveniently administered in unit any suitable dosage form, including but not limited to one containing 7 to 3000 mg, preferably 70 to 1400 mg of active ingredient per unit dosage form. An oral dosage of 50-1000 mg is usually convenient, including in one or multiple dosage forms of 50, 100, 200, 250, 300, 400, 500, 600, 700, 800, 900 or 1000 mg. Lower doses may be used, for example from 10-100 mg, 1-50 mg, 0.1-50 mg, 0.1-20 mg, or 0.1-10.0 mg.

Ideally the active ingredient should be administered to achieve peak plasma concentrations of the active compound of from about 0.2 to 70 μM, preferably about 1.0 to 10 μM. This may be achieved, for example, by the intravenous injection of a 0.1 to 5% solution of the active ingredient, optionally in saline, or administration as a bolus of the active ingredient.

In particularly preferred embodiments according to the present invention, the compounds and compositions are used to treat, prevent or delay the onset of Flaviviridae infections. Preferably, to treat, prevent or delay the onset of infection, the compositions will be administered in oral dosage form in amounts ranging from about 250 micrograms up to about 1 gram or more at least once a day, preferably, or up to four times a day. The present compounds are preferably administered orally, but may be administered parenterally, topically or in suppository form.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

In certain pharmaceutical dosage forms, the prodrug form of the compound, especially including acylated (acetylated or other) and ether derivatives, phosphate esters and various salt forms of the present compounds, is preferred. One of ordinary skill in the art will recognize how to readily modify the present compound to a prodrug form to facilitate delivery of active compound to a targeted site within the host organism or patient. The artisan also will take advantage of favorable pharmacokinetic parameters of the prodrug form, where applicable, in delivering the desired compound to a targeted site within the host organism or patient to maximize the intended effect of the compound in the treatment of Flaviviridae infection (including HCV infection).

To prepare the pharmaceutical compositions according to the present invention, a therapeutically effective amount of one or more of the compounds according to the present invention is preferably mixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated for sustained release by standard techniques. The use of these dosage forms may significantly impact the bioavailability of the compounds in the patient.

For parenteral formulations, the carrier will usually comprise sterile water or aqueous sodium chloride solution, though other ingredients, including those that aid dispersion, also may be included. Where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens or liposomes targeted to infected cells with monoclonal antibodies to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present invention. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

The compounds according to the present invention, because of their low toxicity to host cells in certain instances, may be advantageously employed prophylactically to prevent Flaviviridae infection or to prevent the occurrence of clinical symptoms associated with the viral infection. Thus, the present invention also encompasses methods for the prophylactic treatment of viral infection, and in particular Flaviviridae infection. In this aspect, according to the present invention, the present compositions are used to prevent or delay the onset of a Flaviviridae infection (including HCV). This prophylactic method comprises administration to a patient in need of such treatment, or who is at risk for the development of HCV disease, an amount of a compound according to the present invention effective for alleviating, preventing or delaying the onset of the viral infection. In the prophylactic treatment according to the present invention, it is preferred that the antiviral compound utilized should be low in toxicity and preferably non-toxic to the patient. It is particularly preferred in this aspect of the present invention that the compound that is used should be maximally effective against the virus and should exhibit a minimum of toxicity to the patient. In the case of HCV infection, compounds according to the present invention, which may be used to treat these disease states, may be administered within the same dosage range for therapeutic treatment (i.e., about 250 micrograms up to 1 gram or more from one to four times per day for an oral dosage form) as a prophylactic agent to prevent the proliferation of a Flaviviridae infection, or alternatively, to prolong the onset of a Flaviviridae infection, which manifests itself in clinical symptoms.

VI. PROCESSES FOR THE PREPARATION OF ACTIVE COMPOUNDS

A method for the facile preparation of 2',3'-dideoxynucleosides and their triphosphates is also provided. The method includes condensation of a chiral, non-carbohydrate intermediate 1-O-acetyl-5-O-(tert-butyldiphenylsilyl)-2,3-dideoxy-2-(phenylselenenyl)-α/β-L-erythro-pento-furanose (6), which can be prepared from D-glutamic acid, with a silylated pyrimidine base, followed by reduction and deprotection, to afford a number of β-L-2',3'-dideoxynucleosides. The corresponding D-enantiomers can be synthesized using L-glutamic acid as a starting material.

The 2',3'-dideoxynucleosides disclosed herein can be prepared as described in detail below, or by other assays known to those skilled in the art. For example, such methods are described in the following references: Driscoll, J. S., Marquez, V. E., Kim, C.-H., Kelley, J. A. (1988) U.S. Pat. No. 4,788,181; Amino, Y., Iwagami, H. (1992) U.S. Pat. No. 5,106,962; Jung, M. E., Gardiner, J. M. (1993) U.S. Pat. No. 5,220,003; Lin, T.-S., Cheng, Y.-C. (1997) U.S. Pat. No. 5,631,239; Okabe, M., Sun, R.-C., Tam, S. Y.-K., Todaro, L. J., Coffen, D. L. (1988) *J. Org. Chem.* 53, 4780-4786; Beach, J. W., Kim, H. O., Jeong, L. S., Namoalli, S., Islam, Q., Ahn, S. K., Babu, J. R., Chu, C. K. (1992) *J. Org. Chem.* 57, 3887-3894.

The present invention is further illustrated in the following examples. It will be understood by one of ordinary skill in the art that these examples are in no way limiting and that variations of detail can be made without departing from the spirit and scope of the present invention.

EXAMPLES

Melting points were determined in open capillary tubes on an Electrothermal digit melting point apparatus and are uncorrected. The UV absorption spectra were recorded on an Uvikon 931 (KONTRON) spectrophotometer in ethanol. $^1$H-NMR spectra were run at room temperature using a Varian Unity Plus 400 spectrometer. Chemical shifts are given in ppm downfield from internal tetramethylsilane as reference. Deuterium exchange, decoupling experiments or 2D-COSY were performed in order to confirm proton assignments. Signal multiplicities are represented by s (singlet), d (doublet), dd (doublet of doublets), t (triplet), q (quadruplet), br (broad), m (multiplet). All J-values are in Hz. FAB mass spectra were recorded in the positive-(FAB>0) or negative-(FAB<0) ion mode on a JEOL DX 300 mass spectrometer. The matrix was 3-nitrobenzyl alcohol (NBA) or a mixture (50:50, v/v) of glycerol and thioglycerol (GT). Specific rotations were measured on a Perkin-Elmer 241 spectropolarimeter (path length 1 cm) and are given in units of $10^{-1}$ deg cm$^2$ g$^{-1}$. Elemental analyses were performed by Atlantic Microlab Inc. (Norcross, Ga.). Analyses indicated by the symbols of the elements or functions were within ±0.4% of theoretical values. Thin layer chromatography was performed on Whatman PK5F silica-gel plates, visualization of products being

Example 1

(R)-(−)-5-Oxo-2-tetrahydrofurancarboxylic acid (2)

To a mixture of D-glutamic acid (1, 25 g, 170 mmol) in water (67 mL) and conc. HCl (35 mL) at 0° C. with stirring was added a solution of $NaNO_2$ (17.5 g, 253.6 mmol) in water (37.5 mL) over a period of 4 h, and then the resulting clear solution was stirred at room temperature overnight. After removal of the solvent by evaporation in vacuo, the residue was treated with EtOAC (80 mL) and filtered. The filtrate was dried over $Na_2SO_4$, and concentrated. The residue, after crystallization from EtOAc/benzene/hexane, afforded the title compound 2 as a white crystalline solid (12.63 g, 57%). M.P. 71-73° C.; $^1H$ NMR (400 MHz, $CD_3OD$) δ 4.20 (m, 1H, CHO), 1.8-2.3 (m, 4H, $CH_2CH_2$).

Example 2

(R)-(−)-Dihydro-5-(hydroxymethyl)-2(3H)-furanone (3)

To a solution of 2 (10 g, 76.85 mmol) in anhydrous THF (200 mL) at 0° C. was slowly added $BH_3$—$SMe_2$ (2 M solution in THF, 46.1 mL, 92.2 mmol) over a period of 10 min. The reaction solution was stirred at 0° C. for 3 h under nitrogen, followed by the slow addition of anhydrous MeOH (20 mL). After removal of the solvent, the residue was purified by flash chromatography on silica gel, eluting with $CH_2Cl_2$/MeOH (95:5) to give the title compound 3 as a colorless oil (8.52 g, 95%). $^1H$ NMR ($CDCl_3$) δ 4.66-4.65 (m, 1H, H-5), 3.95-3.91 (m, 1H, $CH_2OH$), 3.72-3.65 (m, 1H, $CH_2OH$), 2.65-2.57 (m, 2H, H-3), 2.30-2.17 (m, 3H, H-4, OH).

Example 3

(R)-5-[(tert-Butyldiphenylsilyl)hydroxymethyl]-dihydro-2(3H)-furanone (4)

To a solution of 3 (7.0 g, 60 mmol) and imidazole (9.19 g, 135 mmol) in anhydrous DMF (70 mL) was added tert-butyldiphenylsilyl chloride (18.14 g, 66 mmol, 17.2 mL), and the solution was stirred at room temperature under nitrogen atmosphere for 1 h. After removal of the solvent by evaporation, the residue was dissolved in $CHCl_3$, washed with water and brine, dried ($Na_2SO_4$), filtered, and concentrated. After crystallization from hexane, the oily residue gave the title compound 4 as a white crystalline solid (20.8 g, 98%). M.P. 76° C.; $^1H$ NMR ($CDCl_3$) δ 7.68-7.65 (m, 4H, arom.), 7.47-7.39 (m, 6H, arom.), 4.63-4.61 (m, 1H, H-5), 3.90-3.87 (dd, J=3 & 11 Hz, 1H, $CH_2OH$), 3.70-3.67 (dd, J=3 & 11 Hz, 1H, $CH_2OH$), 2.69-2.65 (m, 1H, H-3), 2.56-2.52 (m, 1H, H-3), 2.32-2.23 (m, 2H, H-4), 1.06 (s, 9H, t-Bu).

Example 4

(5R,3S)-5-[(tert-Butyldiphenylsilyl)hydroxymethyl]-dihydro-3-(phenylselenenyl)-2(3H)-furanone (5)

To a solution of 4 (5 g, 14.1 mmol) in anhydrous THF (50 mL) at −78° C. was added lithium bis(trimethylsilyl)amide (1 M solution in THF, 15.8 mL, 15.8 mmol) over a period of 10 min. After being stirred at −78° C. for 1 h, $Me_3SiCl$ (1.918 g, 17.65 mmol) was added dropwise, and the reaction mixture was allowed to warm to room temperature. After being stirred at room temperature for 30 min, the mixture was cooled to −78° C., and a solution of PhSeBr (5 g, 21.19 mmol) in anhydrous THF (25 mL) was added rapidly. The mixture was diluted with ether (50 mL), washed with water until the color of organic layer changed from dark brown to light yellow, dried ($Na_2SO_4$), filtered, and evaporated. The resulting oily residue [containing 3S (α, 5) and 3R (β) isomers; TLC: hexane/EtOAc, 10:1; $R_f$=0.42 and 0.28, respectively] was purified by flash chromatography on silica gel, eluting with hexane/EtOAc (99:1 to 95:5) to give the title compound 5 as a light yellow oil (4.093 g, 57%). $^1H$ NMR ($CDCl_3$) δ 7.69-7.60 (m, 6H, arom.), 7.46-7.30 (m, 9H, arom.), 4.37-4.34 (m, 1H, H-5), 4.12-4.08 (m, 1H, H-3), 3.86-3.82 (dd, J=3 & 11 Hz, 1H, $CH_2OH$), 3.62-3.59 (dd, J=3 & 11 Hz, 1H, $CH_2OH$), 2.73-2.67 (m, 1H, H-4), 2.32-2.28 (m, 1H, H-4), 1.02 (s, 9H, t-Bu).

Example 5

1-O-Acetyl-5-O-(tert-butyldiphenylsilyl)-2,3-dideoxy-2-(phenylselenenyl)-α/β-L-erythro-pentofuranose (6)

To a stirred solution of 5 (13.68 g, 26.88 mmol) in anhydrous toluene (120 mL) at −78° C. was added diisobutylaluminum hydride (1 M solution in toluene, 43 mL, 43 mmol), and the solution was stirred at −78° C. for 2 h under an argon atmosphere. The reaction was quenched by addition of anhydrous MeOH (10 mL), and the mixture was allowed to warm to RT. After stirring at room temperature for 30 min, EtOAc (50 mL) and water (50 mL) were added. The resulting white precipitate was filtered, and the aqueous layer was extracted with EtOAc. The combined organic phase was washed with water and brine, dried ($Na_2SO_4$), filtered, and evaporated. The resulting oily residue was dissolved in anhydrous $CH_2Cl_2$ (60 mL), and cooled to 0° C. 4-Dimethylaminopyridine (5 mg) and pyridine (15 mL) were added, followed by $Ac_2O$ (8.22 g, 80.64 mmol). The mixture was stirred at 0° C. for 30 min, then at room temperature overnight. Evaporation of the solvent in vacuo afforded the title compound 6 as a clear yellow oil (13.76 g, 92%). This crude product was used directly without further purification. $^1H$ NMR ($CDCl_3$) δ 7.69-7.55 (m, 6H, arom.), 7.44-7.25 (m, 9H, arom.), 6.47-6.46 (d, H-1), 6.28 (s, H-1), 4.47-4.34 (m, 1H, H-4), 3.82-3.54 (m, 3H, H-5, H-2), 2.50-1.99 (m, 2H, H-3), 2.12, 1.86 (2s, 3H, $CH_3CO$), 1.05, 1.96 (2s, 9H, t-Bu).

Example 6

β-L-5'-O-(tert-Butyldiphenylsilyl)-2',3'-dideoxy-5-fluoro-2'-phenylselenenyl)cytidine (7a, R═$NH_2$, X═F)

A suspension of 5-fluorocytosine (1.61 g, 12.5 mmol) and $(NH_4)_2SO_4$ (165 mg, 1.25 mmol) in hexamethyldisilazane (20 mL) was heated at reflux for 2 h under an argon atmosphere, and then evaporated to dryness in vacuo. To the residue was added a solution of 6 (5.53 g, 10.0 mmol) in anhydrous 1,2-dichloroethane (25 mL), and the mixture was cooled to 5° C. TMSOTf (2.0 mL, 11 mmol) was added, and the resulting solution was stirred at 5° C. for 15 min under an argon atmosphere, then at room temperature for another 30 min. The solution was poured into a mixture of EtOAc and saturated aqueous NaHCO₃ with stirring. The organic layer was separated, washed with saturated NaHCO₃ solution, water and brine, dried (Na₂SO₄), filtered, and concentrated. The residue was purified by flash chromatography on silica gel eluting with CH₂Cl₂/MeOH (99:1 to 96:4) to give 7a as a white solid (5.23 g, 84%). M.P. 163-164° C.; $^1$H NMR (CDCl₃) δ 7.95 (d, J=6.4 Hz, 1H, H-6), 7.67-7.62 (m, 6H, arom.), 7.47-7.25 (m, 9H, arom.), 6.90 (bs, 1H, NH), 6.15-6.14 (m, 1H, H-1'), 5.40 (bs, 1H, NH), 4.32-4.30 (m, 1H, H-4'), 4.12-4.08 (m, 1H, H-5'a), 3.84-3.83 (m, 1H, H-2'), 3.65 (dd, J=2.4 & 11.2 Hz, 1H, H-5'b), 2.45-2.42, 2.01-1.98 (2m, 2H, H-3'), 1.08 (s, 9H, t-Bu); $^{13}$C NMR (CDCl₃) (157.0, 156.8, 153.3, 137.3, 135.6, 135.5, 135.4, 134.9, 132.6, 132.3, 130.1, 130.0, 129.2, 128.3, 127.9, 127.4, 125.5, 125.2, 91.0, 80.2, 64.8, 45.4, 32.3, 26.9, 19.2.

In an analogous manner to the preparation of 7a, β-L-5'-O-(tert-butyldiphenylsilyl)-2',3'-dideoxy-2'-(phenylselenenyl)cytidine (7b, R=NH₂, X=H) was prepared in 76% yield. $^1$H NMR (CDCl₃) δ 8.29 (d, J=7.4 Hz, 1H, H-6), 7.69-7.62 (m, 6H, arom.), 7.48-7.25 (m, 9H, arom.), 7.10 (d, J=7.4 Hz, 1H, H-5), 6.80 (bs, 1H, NH), 6.15-6.14 (m, 1H, H-1'), 5.40 (bs, 1H, NH), 4.32-4.30 (m, 1H, H-4'), 4.10 (m, 1H, H-5'a), 3.83 (m, 1H, H-2'), 3.65 (m, 1H, H-5'b), 2.45-2.42, 2.01-1.98 (2m, 2H, H-3'), 1.08 (s, 9H, t-Bu).

In an analogous manner to the preparation of 7a, β-L-5'-O-(tert-butyldiphenylsilyl)-2',3'-dideoxy-5-fluoro-2'-(phenylselenenyl)uridine (7c, R=OH, X=F) was prepared in 66% yield. M.P. 69-70° C.; $^1$H NMR (CDCl₃) δ 8.12 (bs, 1H, NH), 7.74 (d, J=6.0 Hz, 1H, H-6), 7.66-7.58 (m, 6H, arom.), 7.49-7.26 (m, 9H, arom.), 6.13-6.11 (m, 1H, H-1'), 4.25-4.23 (m, 1H, H-4'), 4.05-4.03 (m, 1H, H-2'), 3.75-3.71, 3.67-3.63 (2m, 2H, H-5'), 2.49-2.45, 2.15-2.07 (2m, 2H, H-3'), 1.11 (s, 9H, t-Bu).

In an analogous manner to the preparation of 7a, β-L-5'-O-(tert-butyldiphenylsilyl)-2',3'-dideoxy-2'-(phenylselenenyl)uridine (7d, R=OH, X=H) was prepared in 64% yield. $^1$H NMR (CDCl₃) δ 8.55 (bs, 1H, NH), 7.90-7.20 (m, 16H, arom., H-6), 6.15 (d, J=5.2 Hz, 1H, H-1'), 5.28 (d, J=7.7 Hz, 1H, H-5), 4.25-4.23 (m, 1H, H-4'), 4.10 (m, 1H, H-2'), 3.75-3.65 (m, 2H, H-5'), 2.52-2.47, 2.17-2.11 (2m, 2H, H-3'), 1.08 (s, 9H, t-Bu).

Example 7

β-L-5'-O-(tert-Butyldiphenylsilyl)-2',3'-dideoxy-5-fluorocytidine (8a, R=NH₂, X=F)

A suspension of 7a (4.976 g, 8 mmol), Et₃B (1 M solution in hexane, 8.8 mL, 8.8 mmol), and n-Bu₃SnH (3.23 mL, 12 mmol) in anhydrous benzene (40 mL) was stirred at room temperature under argon atmosphere for 5 h. After evaporation of the solvent, the residue was purified by flash chromatography on silica gel eluting with CH₂Cl₂/MeOH (99:1 to 96:4) to give the title compound 8a as a pale yellow foam (3.66 g, 98%). $^1$H NMR (CDCl₃) δ 8.14 (d, J=6.4 Hz, 1H, H-6), 7.71-7.66 (m, 4H, arom.), 7.49-7.38 (m, 6H, arom.), 6.04 (m, 1H, H-1'), 4.17-4.12 (m, 1H, H-4'), 4.12-4.08 (m, 1H, H-5'a), 3.73-3.69 (m, 1H, H-5'b), 2.54-2.44, 2.18-2.09 (2 m, 2H, H-3'), 2.05-1.95, 1.89-1.82 (2 m, 2H, H-2'), 1.10 (s, 9H, t-Bu).

In an analogous manner to the preparation of 8a, β-L-5'-O-(tert-butyldiphenylsilyl)-2',3'-dideoxycytidine (8b, R=NH₂, X=H) was prepared in 93% yield. $^1$H NMR (CDCl₃) δ 8.37 (d, J=8.2 Hz, 1H, H-6), 7.73-7.32 (m, 10H, arom.), 7.20 (d, J=8.2 Hz, 1H, H-5), 6.10 (m, 1H, H-1'), 4.27-4.00 (m, 2H, H-4', H-5'a), 3.75 (m, 1H, H-5'b), 2.55-1.78 (m, 4H, H-2', H-3'), 1.10 (s, 9H, t-Bu).

In an analogous manner to the preparation of 8a, β-L-5'-O-(tert-butyldiphenylsilyl)-2',3'-dideoxy-5-fluorouridine (8c, R=OH, X=F) was prepared in 91% yield. M.P. 69-70° C.; $^1$H NMR (CDCl₃) δ 8.11 (bs, 1H, NH), 7.75 (d, J=6.0 Hz, 1H, H-6), 7.76-7.30 (m, 10H, arom.), 6.12 (m, 1H, H-1'), 4.12 (m, 1H, H-4'), 4.09, 3.74 (2 m, 2H, H-5'), 2.50-2.03 (m, 4H, H-2', H-3'), 1.10 (s, 9H, t-Bu).

In an analogous manner to the preparation of 8a, β-L-5'-O-(tert-butyldiphenylsilyl)-2',3'-dideoxyuridine (8d, R=OH, X=H) was prepared in 92% yield. $^1$H NMR (CDCl₃) δ 9.4 (bs, 1H, NH), 7.94 (d, J=8.2 Hz, 1H, H-6), 7.80-7.30 (m, 10H, arom.), 6.20 (m, 1H, H-1'), 5.42 (d, J=8.2 Hz, 1H, H-5), 4.10 (m, 1H, H-4'), 4.08, 3.73 (2 m, 2H, H-5'), 2.50-2.00 (m, 4H, H-2', H-3'), 1.09 (s, 9H, t-Bu).

Example 8

β-L-2',3'-Dideoxy-5-fluorocytidine (9a, R=NH₂, X=F)

To a solution of 8a (389 mg, 0.83 mmol) in THF (4 mL) was added a solution of tetrabutylammonium fluoride (1M solution in THF, 0.83 mL, 0.83 mmol), and the mixture was stirred at room temperature for 2 h. After removal of the solvent by evaporation, the residue was purified by flash chromatography on silica gel eluting with CH₂Cl₂/MeOH (9:1) to give the title compound 9a as a white crystalline solid (161 mg, 85%). $^1$H NMR (DMSO-d₆) δ 8.29 (d, J=7.3 Hz, 1H, H-6), 7.65, 7.41 (2bs, 2H, NH₂), 5.86 (m, 1H, H-1'), 5.16 (t, J=5.1 Hz, 1H, OH), 4.04 (m, 1H, H-4'), 3.77-3.72, 3.57-3.52 (2 m, 2H, H-5'), 2.30-2.21, 1.91-1.80 (2 m, 4H, H-2', H-3').

In an analogous manner to the preparation of 9a, β-L-2',3'-dideoxycytidine (9b, R=NH₂, X=H) was prepared in 87% yield. M.P. 210-212° C.; $^1$H NMR (DMSO-d₆) δ 7.90 (d, J=7.2 Hz, 1H, H-6), 7.02 (bs, 2H, NH₂), 5.92 (m, 1H, H-1'), 5.71 (d, J=7.2 Hz, 1H, H-5), 4.96 (t, J=7.2 Hz, 1H, OH), 4.00 (m, 1H, H-4'), 3.66, 3.56 (2 m, 2H, H-5'), 2.22 (m, 2H, H-2'), 1.76, 1.85 (2 m, 2H, H-3').

In an analogous manner to the preparation of 9a, β-L-2',3'-dideoxy-5-fluorouridine (9c, R=OH, X=F) was prepared in 90% yield. M.P. 109-111° C.; $^1$H NMR (DMSO-d₆) δ 11.7 (bs, 1H, NH), 8.36 (d, J=7.2 Hz, 1H, H-6), 5.92 (m, 1H, H-1'), 5.12 (t, 1H, OH), 4.10 (m, 1H, H-4'), 3.80-3.55 (m, 2H, H-5'), 2.45-1.85 (m, 4H, H-2', H-3').

In an analogous manner to the preparation of 9a, β-L-2',3'-dideoxyuridine (9d, R=OH, X=H) was prepared in 86% yield. M.P. 118-120° C.; $^1$H NMR (DMSO-d₆) δ 11.2 (bs, 1H, NH), 7.95 (d, J=7.9 Hz, 1H, H-6), 5.95 (m, 1H, H-1'), 5.50 (d, J=7.9 Hz, 1H, H-5), 5.02 (t, 1H, OH), 4.00 (m, 1H, H-4'), 3.60 (m, 2H, H-5'), 2.40-1.70 (m, 4H, H-2', H-3').

Example 9

β-L-2',3'-Dideoxy-5-fluorocytidine triphosphate, triethylammonium salt (10a, R=NH₂, X=F)

To a solution of 9a (10 mg) in anhydrous DMF (0.3 mL) and pyridine (0.1 mL) was added a solution of 2-chloro-4H-1,3,2-benzodioxaphosphorin-4-one (salicylchlorophosphite) in anhydrous 1,4-dioxane (1 M, 0.05 mL). The resulting solution was stirred at room temperature for 15 min, and then a solution of bis(tributylammonium)pyrophosphorate in anhydrous DMF (1 M, 0.12 mL) was added, followed by Bu₃N (0.05 mL). After stirring at room temperature for 15 min, a solution of I₂/H₂O/pyridine/THF was added to the above solution dropwise until the iodine color persisted (about 0.5 mL), and the mixture was concentrated (below 40°

C.) in vacuo. The residue was dissolved in water (2 mL), washed with $CH_2Cl_2$ (3×1 mL), filtered, and purified by HPLC [column: DIONEX NucleoPac PA-100 (9×250); buffer A: 0.05 M TEAB; buffer B: 0.5 M TEAB; flow rate: 7.5 mL/min; gradient: increasing buffer B from 0% at 0 min to 50% at 10 min, 100% at 12 min and maintained till 17 min]. Collection and lyophilization of the peak which had retention time of 8~9 min afforded the title compound 10a as a colorless syrup. The purity of compound 10a, as shown by HPLC [column: DIONEX NucleoPac PA-100 (4×250); buffer A: 25 mM Tris/Cl; buffer B: 0.5 M NaCl in 25 mM Tris/Cl; flow rate: 1.5 mL/min; gradient: starting from 100% buffer A, by increasing buffer B from 0% at 1 min to 50% at 15 min, 80% at 18 min and maintained it till 23 min, retention time 8.9 min]: >98%. MS ($FAB^-$) m/e 468 ($[M-H]^-$).

In an analogous manner to the preparation of 10a, β-L-2',3'-dideoxycytidine triphosphate, triethylammonium salt (10b, R=$NH_2$, X=H) was prepared. MS ($FAB^-$) m/e 450 ($[M-H]^-$).

In an analogous manner to the preparation of 10a, β-L-2',3'-dideoxy-5-fluorouridine triphosphate, triethylammonium salt (10c, R=OH, X=F) was prepared. MS ($FAB^-$) m/e 469 ($[M-H]^-$).

In an analogous manner to the preparation of 10a, β-L-2',3'-dideoxyuridine triphosphate, triethylammonium salt (10d, R=OH, X=H) was prepared. MS ($FAB^-$) m/e 451 ($[M-H]^-$).

Example 10

HCV Polymerase Expression and Purification

The HCV NS5B gene was amplified from a genotype 1A, clone, p134/pBRTM 2029-3011 (ΔAvrII). The primers used added a methionine and alanine to the N terminus and truncated the C-terminal 21 amino acids, replacing them with a hexahistidine tag, which allowed increased soluble product in *E. coli* and metal affinity purification. The PCR product was cloned into the pET32a expression construct (Novagen) at the NcoI and BamHI sites and the resultant plasmid (pRSK1) was sequenced by the Stanford PAN facility using standard methods. BL 1 (DE3)pLysS cells (Novagen) were transformed by pRSK1 and grown at 37° C. to an optical density of 0.1, at which time the cells were switched to room temperature. At an optical density of 0.3-0.5, isopropyl-β-D-thiogalactopyanoside was added to a final concentration of 0.5 mM and the cells were harvested after 6 h. The cell pellet was frozen, thawed and resuspended in buffer containing 50 mM sodium phosphate pH 7.0, 10% glycerol, 0.3 M NaCl, 2 mM β-mercaptoethanol, 0.5% β-octyl-glucoside. The cell extract was sonicated, and cellular debris removed by centrifugation. The extract was incubated batch-wise with Talon metal affinity resin (Clontech), washed extensively with the above buffer, and then poured into a column for a stepwise imidazole elution. The polymerase, referred to as NS5Bt, eluted specifically between 70 mM and 250 mM imidazole and was ~90% pure.

Example 11

HCV Polymerase Inhibition Assay

RdRp assays were a modification of the assays described in Kao et al. (Kao, C, C.; Yang, X.; Kline, A.; Wang, Q. M.; Barket, D.; Heinz, B. A. (2000) *J. Virol.* 74, 11121-11128). The template used allows for de novo synthesis and has its 3' termini blocked by puromycin, which largely prevents the high molecular weight product from forming and allows for predominantly 24- and 25-nucleotide products to be seen. Each reaction contained 50 mM Hepes-NaOH pH 8.0, 0.65 μM template, 0.1 μM purified NS5Bt described above, 250 μM GTP, 5 μM UTP, 0.6 μM CTP, and 1 μM [αP32] ATP, 0.5 mM MnCl2, 7 mM $MgCl_2$, 18 mM DTT, and the stated concentration of the analog. Reaction mixes were incubated at 27° C. for 45 min. Reactions were terminated by the addition of ⅕ the volume of 5× proteinase K mix (250 μg proteinase K/ml [Sigma, St Louis, Mo.], 375 mM Hepes-NaOH pH 8, 0.5% SDS, 25 mM EDTA) and incubated for 10 min at 37° C. Reactions were then precipitated with isopropanol, and glycogen as a carrier, and washed twice with 70% ethanol to remove salt. The RNA was resuspended in formamide loading buffer, heated to 65° C. for 3 min and loaded on a 20% acrylamide/7 M urea/TBE denaturing gel and separated by electrophoresis at 50° C. Quantification of bands was performed using Phosphoimager analysis.

Example 12

BVDV Inhibition Assay

One of the best characterized members of the Pestivirus genus is BVDV. BVDV and HCV share at least three common features: (1) they both undergo IRES-mediated translation; (2) NS4A cofactor is required by their NS3 serine protease; and (3) they undergo similar polyprotein processing within the non-structural region, especially at the NS5A and NS5B junction site. Therefore, the BVDV replication system was used for the discovery of anti-Flaviviridae compounds. The compounds described herein are active against Pestiviruses, Hepaciviruses and/or Flaviviruses.

Maldin-Darby bovine kidney (MDBK) cells were grown and maintained in a modified eagle medium (DMEM/F12; GibcoBRL), supplemented with 10% heat-inactivated horse serum at 37° C. in a humidified, 5% $CO_2$, incubator. BVDV, strain NADL, causes a cytopathogenic effect (CPE) after infection of these cells.

MDBK-cells, grown in DMEM/F12+10% horse serum (HS), were isolated using standard techniques using trypsin-EDTA. Cells were seeded in a 96-well plate at $5\times10^4$ cells/well, with test compound (20 micromolar (μM) concentration) to give a total volume of 100 microliters (μL). After 1 hr, the medium was removed and the cells were infected at a multiplicity of infection (MOI) of 0.02 or 0.002 in a total volume of 50 μL for 45 minutes. Thereafter, the virus was removed and the cells were washed twice with assay medium (100 μL). Finally, the infected cells were incubated in a total volume of 100 μL containing the test compound at 40 or 100 μM concentration. After 22 h, the cell supernatant was collected by removing the cellular debris by low-speed centrifugation, and subsequently tested for the presence of virus in a quantitative manner.

Example 13

Cytotoxicity Testing of Candidate Anti-Flaviviridae Compounds

Cytotoxicity testing can be carried out according to standard methods. Briefly, cells are seeded in 96-well plates at various concentrations (dependent on cell type, duration of assay), typically at $5\times10^3$ cells per well, in the presence of increasing concentrations of the test compound (0, 1, 10, 33, and 100 μM). After a three day-incubation, cell viability and mitochondrial activity are measured by adding the MTS-dye (Promega), followed by a 3 h incubation. Then, plates containing the dye are read at 490 nm. Such methodologies are well described and available from the manufacturer (Promega).

This invention has been described with reference to its preferred embodiments. Variations and modifications of the invention, will be obvious to those skilled in the art from the foregoing detailed description of the invention. It is intended that all of these variations and modifications be included within the scope of this invention.

We claim:

1. A pharmaceutical composition for the treatment of an HCV infection in a host, comprising an effective treatment amount of a 2',3'-dideoxynucleoside of the formula:

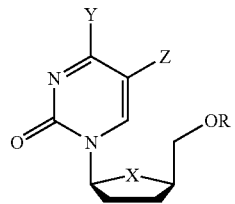

or a pharmaceutically acceptable salt thereof, wherein
 (i) X is S=O, SO$_2$, NR$^1$, N$^+$R$^1$R$^2$, CHF or CR$^3$R$^4$;
   R$^1$ and R$^2$ are independently C$_{2-6}$ alkenyl, C$_{2-6}$ alkynyl, or C$_{3-8}$ cycloalkyl;
   R$^3$ and R$^4$ are independently hydrogen, halogen (F, Cl, Br, or I), OH or OR$^5$, with the proviso that R$^3$ and R$^4$ are not both hydrogen;
   R$^5$ is hydrogen, an alkyl, an acyl, or a silyl;
 (ii) Y is NH$_2$, NHR$^6$, NR$^6$R$^7$, OH or OR$^8$
   each R$^6$, R$^7$ and R$^7$ is independently H, C$_{1-6}$ alkyl, C$_{2-6}$ alkenyl, C$_{2-6}$ alkynyl, C$_{3-8}$ cycloalkyl, cyclopropyl, or C$_{2-6}$ acyl;
 (iii) Z is chosen from hydrogen, halogen (F, Cl, Br, or I), C$_{1-6}$ alkyl, C$_{2-6}$ alkenyl, C$_{2-6}$ alkynyl, CN, CF$_3$, N$_3$, NO$_2$, aryl, heteroaryl and COR$^9$;
   R$^9$ is chosen from H, OH, SH, C$_{1-6}$ alkyl, C$_{1-6}$ aminoalkyl, C$_{1-6}$ alkoxy and C$_{1-6}$ thioalkyl; and
 (iv) R is phosphate; acyl; —C(O)R$^{10}$, alkyl; sulfonate ester; sulfonyl; a lipid; an amino acid; a carbohydrate; a peptide; a cholesterol; or other pharmaceutically acceptable leaving group;
   R$^{10}$ is a C$_{1-6}$ alkyl, C$_{2-6}$ alkenyl, C$_{2-6}$ alkynyl, aryl, monophosphate, diphosphate, triphosphate, or —P(O)(OR$^{11}$)$_2$;
   each R$^{11}$ is independently hydrogen, C$_{1-6}$ alkyl, C$_{2-6}$ alkenyl, C$_{2-6}$ alkynyl or a hydroxyl-protecting group;
together with pharmaceutically acceptable carrier.

2. The pharmaceutical composition of claim 1, wherein Z is not hydrogen.

3. The pharmaceutical composition of claim 1, wherein Z is a halogen (F, Cl, Br, or I).

4. The pharmaceutical composition of claim 3, wherein Z is F.

5. The pharmaceutical composition of claim 1, wherein the 2',3'-dideoxynucleoside is in the β-L-configuration.

6. The pharmaceutical composition of claim 5, wherein the β-L-2',3'-dideoxynucleoside is enantiomerically enriched.

7. The pharmaceutical composition of claim 5, wherein the β-L-2',3'-dideoxynucleoside is substantially free of the β-D-2',3'-dideoxynucleoside.

8. The pharmaceutical composition of claim 5, wherein the β-L-2',3'-dideoxynucleoside is in isolated form.

9. A pharmaceutical composition for the treatment of an HCV infection in a host, comprising an effective amount of a compound of the formula:

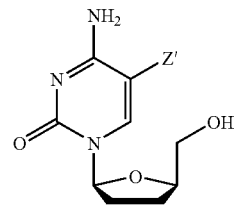

or a pharmaceutically acceptable salt, wherein
  Z' is CF$_3$ or N$_3$;
together with a pharmaceutically acceptable carrier.

10. A pharmaceutical composition for the treatment of an HCV infection in a host, comprising an effective amount of a compound of the formula:

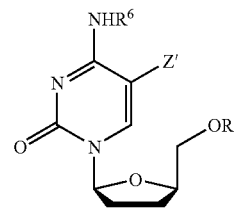

or a pharmaceutically acceptable salt thereof, wherein
 (i) R$^6$ is C$_{1-6}$ alkyl, C$_{2-6}$ alkenyl, C$_{2-6}$ alkynyl, C$_{3-8}$ cycloalkyl, cyclopropyl, or C$_{2-6}$ acyl; and
 (ii) R is hydrogen, phosphate, acyl, —C(O)R$^{10}$, alkyl, sulfonate ester, sulfonyl, a lipid, an amino acid, a carbohydrate, a peptide, a cholesterol, or other pharmaceutically acceptable leaving group;
 (iii) Z' is CF$_3$ or N$_3$;
together with a pharmaceutically acceptable carrier.

11. The pharmaceutical composition of claim 10, wherein the β-L-2',3'-dideoxynucleoside is enantiomerically enriched.

12. The pharmaceutical composition of claim 10, wherein the β-L-2',3'-dideoxynucleoside is substantially free of the β-D-2',3'-dideoxynucleoside.

13. The pharmaceutical composition of claim 10, wherein the β-L-2',3'-dideoxynucleoside is in an isolated form.

14. A pharmaceutical composition for reducing the biological activity of a Flaviviridae viral infection in a host comprising an effective amount of a 2',3'-dideoxynucleoside of the formula:

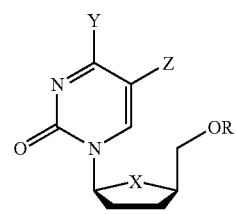

or a pharmaceutically acceptable salt thereof, wherein
 (i) X is S=O, SO$_2$, NR$^1$, N$^+$R$^1$R$^2$, CHF or CR$^3$R$^4$;
   R$^1$ and R$^2$ are independently C$_{2-6}$ alkenyl, C$_{2-6}$ alkynyl, or C$_{3-8}$ cycloalkyl;

R³ and R⁴ are independently hydrogen, halogen (F, Cl, Br, or I), OH or OR⁵, with the proviso that R³ and R⁴ are not both hydrogen;
R⁵ is hydrogen, an alkyl, an acyl, or a silyl;
(ii) Y is $NH_2$, $NHR^6$, $NR^6R^7$, OH or $OR^8$
each R⁶, R⁷ and R⁷ is independently H, $C_{1-6}$ alkyl, $C_{2-6}$ alkenyl, $C_{2-6}$ alkynyl, $C_{3-8}$ cycloalkyl, cyclopropyl, or $C_{2-6}$ acyl;
(iii) Z is chosen from hydrogen, halogen (F, Cl, Br, or I), $C_{1-6}$ alkyl, $C_{2-6}$ alkenyl, $C_{2-6}$ alkynyl, CN, $CF_3$, $N_3$, $NO_2$, aryl, heteroaryl and $COR^9$;
R⁹ is chosen from H, OH, SH, $C_{1-6}$ alkyl, $C_{1-6}$ aminoalkyl, $C_{1-6}$ alkoxy and $C_{1-6}$ thioalkyl; and
(iv) R is phosphate; acyl; —C(O)R¹⁰, alkyl; sulfonate ester; sulfonyl; a lipid; an amino acid; a carbohydrate; a peptide; a cholesterol; or other pharmaceutically acceptable leaving group;
R¹⁰ is a $C_{1-6}$ alkyl, $C_{2-6}$ alkenyl, $C_{2-6}$ alkynyl, aryl, monophosphate, diphosphate, triphosphate, or —P(O)(OR¹¹)₂;
each R¹¹ is independently hydrogen, $C_{1-6}$ alkyl, $C_{2-6}$ alkenyl, $C_{2-6}$ alkynyl or a hydroxyl-protecting group;
together with a pharmaceutically acceptable carrier.

15. The pharmaceutical composition of claim 14, wherein Z is not hydrogen.

16. The pharmaceutical composition of claim 14, wherein Z is a halogen (F, Cl, Br, or I).

17. The pharmaceutical composition of claim 16, wherein Z is F.

18. The pharmaceutical composition of claim 14, wherein the 2',3'-dideoxynucleoside is in the β-L-configuration.

19. A pharmaceutical composition for reducing the biological activity of a Flaviviridae viral infection in a host comprising an effective amount of a compound of the formula:

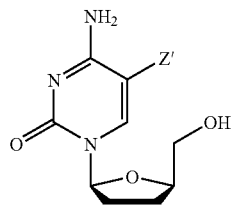

or a pharmaceutically acceptable salt thereof, wherein
Z' is $CF_3$ or $N_3$;
together with a pharmaceutically acceptable carrier.

20. A pharmaceutical composition for reducing the biological activity of a Flaviviridae viral infection in a host comprising an effective amount of a compound of the formula:

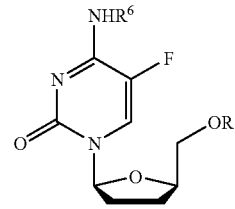

or a pharmaceutically acceptable salt thereof, wherein
(i) R⁶ is H, $C_{1-6}$ alkyl, $C_{2-6}$ alkenyl, $C_{2-6}$ alkynyl, $C_{3-8}$ cycloalkyl, cyclopropyl, or $C_{2-6}$ acyl; and
(ii) R is phosphate; acyl; —C(O)R¹⁰, alkyl; sulfonate ester; sulfonyl; a lipid; an amino acid; a carbohydrate; a peptide; a cholesterol; or other pharmaceutically acceptable leaving group;
(iii) Z' is $CF_3$ or $N_3$;
together with a pharmaceutically acceptable carrier.

21. The pharmaceutical composition according to claim 14, wherein the Flaviviridae viral infection is an HCV infection.

22. The pharmaceutical composition according to claim 1, further comprising one or more other antiviral agent(s).

23. The pharmaceutical composition according to claim 22, wherein the antiviral agent is selected from the group consisting of ribavirin, interferon, PEGASYS (pegylated interferon alfa-2a), INFERGEN (interferon alfacon-1), OMNIFERON (natural interferon), ALBUFERON, REBIF (interferon beta-1a), Omega Interferon, Oral Interferon Alpha, Interferon gamma-1b, Interleukin-10, IP-501, Merimebodib VX-497, AMANTADINE (Symmetrel), HEPTAZYME, IDN-6556, XTL-002, HCV/MF59, CIVACIR, LEVOVIRIN, VIRAMIDINE, ZADAXIN (thymosin alfa-1), CEPLENE (histamine dihydrochloride), VX 950/LY 570310, ISIS 14803, IDN-6556 and JTK 003.

24. The pharmaceutical composition according to claim 1, wherein the host is a human.

25. The pharmaceutical composition according to claim 14, wherein the host is also infected with HIV and/or HBV.

26. The pharmaceutical composition according to claim 25, wherein the host is a human.

* * * * *